United States Patent
Kakkis et al.

(10) Patent No.: US 6,426,208 B1
(45) Date of Patent: Jul. 30, 2002

(54) RECOMBINANT α-L-IDURONIDASE, METHODS FOR PRODUCING AND PURIFYING THE SAME AND METHODS FOR TREATING DISEASES CAUSED BY DEFICIENCIES THEREOF

(75) Inventors: Emil D. Kakkis, Long Beach; Becky Tanamachi, Signal Hill, both of CA (US)

(73) Assignee: Harbor-UCLA Research and Education Institute, Torrance, CA (US)

( * ) Notice: Subject to any disclaimer, the term of this patent is extended or adjusted under 35 U.S.C. 154(b) by 0 days.

(21) Appl. No.: 09/439,923

(22) Filed: Nov. 12, 1999

(51) Int. Cl.$^7$ ............................ C12N 9/00; C12N 9/04; C12N 9/24; C12N 9/26; C12N 9/44
(52) U.S. Cl. ...................... 435/201; 435/183; 435/190; 435/200; 435/206; 435/210
(58) Field of Search ................................ 435/183, 190, 435/200, 201, 210, 206

(56) References Cited

U.S. PATENT DOCUMENTS

| | | | |
|---|---|---|---|
| 3,472,931 A | 10/1969 | Stoughton | |
| 3,891,757 A | 6/1975 | Higuchi | |
| 5,270,051 A | 12/1993 | Harris | |

FOREIGN PATENT DOCUMENTS

| | | |
|---|---|---|
| GB | 1001949 | 8/1965 |
| WO | WO 93/10244 | 5/1993 |
| WO | WO 99/51724 | 10/1999 |
| WO | WO 99/58691 | 11/1999 |

OTHER PUBLICATIONS

Clements, et al., "Human alpha–L–iduronidase 1. Purification, monoclonal and antibody production, native and subunit molecular mass", European Journal of Biochemistry, 152(1):43–49 (1994).

Kakkis, et al., "Enzyme–replacement therapy in mucopolysaccharidosis I.", New England Journal of Medicine, 344(3):182–188 (2001).

Anson, D. S., et al., "Correction of Human Mucopolysaccharidosis Type–VI Fibroblasts with Recombinant N–Acetylgalactosamine–4–Suplphatase," Biochem J.—284:789–794 (1992).

Barton, R. W., et al., "The Hurler Corrective Factor," J. Biol. Chem.—246(24):7773–7779 (1971).

Bielicki, J., et al., "Recombinant Human Iduronate–2–Sulphatase: Correction of Mucopolysaccharidosis–Type II Fibbroblasts and Characterization of the Purified Enzyme," Biochem. J.—289:241–246 (1993).

Friedman, T., "Progress Toward Human Gene Therapy," Science—244:1275–1281 (1989).

Hoogerbrugge, P.M., et al., "Allogeneic Bone Marrow Transplantation for Lysosomal Storage Diseases," Lancet—345:1398 (1995).

Ioannou, Y.A., et al., "Overexpression of Human α–Galactosidase A Results in Its Intacellular Aggregation, Crystallization in Lysosomes, and Selective Secretion," J. Cell Biol.—119(5):1137–1150 (1992).

Kakkis, E.D., et al., "Long–Term and High–Dose Trials of Enzyme Replacement Therapy in the Canine Model of Mucopolysaccharidosis[1],"—58(2):156–157 (1996).

Kakkis, E., et al., "Strong Transcriptional Activation of Translocated C–Myc Genes Occurs Without a Strong Nearby Enhancer or Promoter," Nucleic Acids Res.—16(1):77–96 (1988).

Ledley, F.D., "Clinical Application of Somatic Gene Therapy in Inborn Errors of Metabolism," J. Inherit. Metab. Dis.—13:597–616 (1990).

Lowry, R.B., et al. "An Update on the Frequency of Mucopolysaccharide Syndromes in British Columbia," Human Genetics—85:389–390 (1990).

Myerowitz, R., et al., "Maturation of α–L–Iduronidase in Cultured Human Fibroblasts," J. Biol. Chem.—256(6):3044–3048 (1981).

Moskowitz, S.M., et al., "Cloning and Expression of cDNA Encoding the Human Lysosomal Enzyme, α–L–Iduronidase," FASEB J.—6:A77 (1992).

Nelson, J., "Incidence of the Mucopolysaccharidoses in Northern Ireland," Human Genetics—101:355–358 (1997).

Scriver, C.R., Beaudet, A.L., Sly, W.S. and Valle, D. Eds. The Metabolic Basis of Inherited Disease pp. 1565–1587, McGraw Hill, New York (1989).

Shull, R.M., et al., "Enzyme Replacement in a Canine Model of Hurler Syndrome," Proc. Natl. Acad. Sci., USA—91:12937–12941 (1994).

Stoltzfus, L.J., et al., "Cloning and Characterization of cDNA Encoding Canine α–L–Iduronidase," J. Biol. Chem.—267(10):6570–6575 (1992).

Taylor, J., et al., "α–L–Iduronidase in Normal and Mucopolysaccharidosis—Type–1 Human Skin Fibroblasts," Biochem J.—274:263–268 (1991).

Tolstoshev, P., et al., "Gene Expression Using Retroviral Vectors," Current Opinions Biotech.—1:55–61 (1990).

Tucker, P.W., et al., "Mouse IgA Heavy Chain Gene Sequence: Implications for Evolution of Immunoglobulin Hinge Exons," Proc. Natl. Acad. Sci. USA—78(12):7684–7688 (1981).

Unger, E.G., et al., "Recombinant α–L–Iduronidase: Characterization of the Purified Enzyme and Correction of Mucopolysaccharidosis Type I Fibroblasts," Biochem. J.—304:43–49 (1994).

Primary Examiner—Ponnathapu Achutamurthy
Assistant Examiner—Manjunath N. Rao
(74) Attorney, Agent, or Firm—Albert P. Halluin; Robin C. Chiang; Howrey Simon Arnold & White, LLP

(57) ABSTRACT

The present invention provides a recombinant α-L-iduronidase and biologically active fragments and mutants thereof, methods to produce and purify this enzyme as well as methods to treat certain genetic disorders including-α-L-iduronidase deficiency and mucopolysaccharidosis I (MPS 1).

7 Claims, 15 Drawing Sheets

Sequence Range: 1 to 6200

```
              10         20         30         40         50         60         70
               *          *          *          *          *          *          *
          GACGGATCGG GAGATCTCCC GATCCCCTAT GGTCGACTCT CAGTACAATC TGCTCTGATG CCGCATAGTT 80         90        100        110        120        130        140
               *          *          *          *          *          *          *
          AAGCCAGTAT CTGCTCCCTG CTTGTGTGTT GGAGGTCGCT GAGTAGTGCG CGAGCAAAAT TTAAGCTACA 150        160        170        180        190        200        210
               *          *          *          *          *          *          *
          ACAAGGCAAG GCTTGACCGA CAATTGCATG AAGAATCTGC TTAGGGTTAG GCGTTTTGCG CTGCTTCGCG 220        230        240        250        260        270        280
               *          *          *          *          *          *          *
          ATGTACGGGC CAGATATACG CGTTGACATT GATTATTGAC TAGTTATTAA TAGTAATCAA TTACGGGGTC 290        300        310        320        330        340        350
               *          *          *          *          *          *          *
          ATTAGTTCAT AGCCCATATA TGGAGTTCCG CGTTACATAA CTTACGGTAA ATGGCCCGCC TGGCTGACCG 360        370        380        390        400        410        420
               *          *          *          *          *          *          *
          CCCAACGACC CCCGCCCATT GACGTCAATA ATGACGTATG TTCCCATAGT AACGCCAATA GGGACTTTCC 430        440        450        460        470        480        490
               *          *          *          *          *          *          *
          ATTGACGTCA ATGGGTGGAC TATTTACGGT AAACTGCCCA CTTGGCAGTA CATCAAGTGT ATCATATGCC 500        510        520        530        540        550        560
               *          *          *          *          *          *          *
          AAGTACGCCC CCTATTGACG TCAATGACGG TAAATGGCCC GCCTGGCATT ATGCCCAGTA CATGACCTTA 570        580        590        600        610        620        630
               *          *          *          *          *          *          *
          TGGGACTTTC CTACTTGGCA GTACATCTAC GTATTAGTCA TCGCTATTAC CATGGTGATG CGGTTTTGGC 640        650        660        670        680        690        700
               *          *          *          *          *          *          *
          AGTACATCAA TGGGCGTGGA TAGCGGTTTG ACTCACGGGG ATTTCCAAGT CTCCACCCCA TTGACGTCAA 710        720        730        740        750        760        770
               *          *          *          *          *          *          *
          TGGGAGTTTG TTTTGGCACC AAAATCAACG GGACTTTCCA AAATGTCGTA ACAACTCCGC CCCATTGACG 780        790        800        810        820        830        840
               *          *          *          *          *          *          *
          CAAATGGGCG GTAGGCGTGT ACGGTGGGAG GTCTATATAA GCAGAGCTCT CTGGCTAACT AGAGAACCCA 850        860        870        880        890        900        910
               *          *          *          *          *          *          *
          CTGCTTAACT GGCTTATCGA AATTAATACG ACTCACTATA GGGAGACCCA AGCTTCGCAG AATTCCTGCG 920        930        940        950        960        970        980
               *          *          *          *          *          *          *
          GCTGCTACAG TGTGTCCAGC GTCCTGCCTG GCTGTGCTGA GCGCTGGAAC AGTGGCGCAT CATTCAAGTG 990       1000       1010       1020       1030       1040       1050
               *          *          *          *          *          *          *
          CACAGTTACC CATCCTGAGT CTGGCACCTT AACTGGCACA ATTGCCAAAG TCACAGGTGA GCTCAGATGC
```

FIGURE 1

```
          1060        1070        1080        1090        1100       1110        1120
            *           *           *           *           *          *           *
       ATACCAGGAC  ATTGTATGAC  GTTCCCTGCT  CACATGCCTG  CTTTCTTCCT  ATAATACAGA  TGCTCAACTA 1130        1140        1150        1160        1170       1180        1190
            *           *           *           *           *          *           *
       ACTGCTCATG  TCCTTATATC  ACAGAGGGAA  ATTGGAGCTA  TCTGAGGAAC  TGCCCACAAG  GGAAGGGCAG 1200        1210        1220        1230        1240       1250        1260
            *           *           *           *           *          *           *
       AGGGGTCTTG  CTCTCCTTGT  CTGAGCCATA  ACTCTTCTTT  CTACCTTCCA  GTGAACACCT  TCCCACCCCA 1270        1280        1290        1300        1310       1320        1330
            *           *           *           *           *          *           *
       GGTCCACCTG  CTACCGCCGC  CGTCGGAGGA  GCTGGCCCTG  AATGAGCTCT  TGTCCCTGAC  ATGCCTGGTG 1340        1350        1360        1370        1380       1390        1400
            *           *           *           *           *          *           *
       CGAGCTTTCA  ACCCTAAAGA  AGTGCTGGTG  CGATGGCTGC  ATGGAAATGA  GGAGCTGTCC  CCAGAAAGCT 1410        1420        1430        1440        1450       1460        1470
            *           *           *           *           *          *           *
       ACCTAGTGTT  TGAGCCCCTA  AAGGAGCCAG  GCGAGGGAGC  CACCACCTAC  CTGGTGACAA  GCGTGTTGCG 1480        1490        1500        1510        1520       1530        1540
            *           *           *           *           *          *           *
       TGTATCAGCT  GAAAGCTTGA  TATCGAATTC  CGGAGGCGGA  ACCGGCAGTG  CAGCCCGAAG  CCCCGCAGTC 1550        1560        1570        1580        1590
            *           *           *           *           *
       CCCGAGCACG  CGTGGCC ATG CGT CCC CTG CGC CCC CGC GCC GCG CTG CTG GCG CTC CTG
                           Met Arg Pro Leu Arg Pro Arg Ala Ala Leu Leu Ala Leu Leu>
                        ___a___a___a___a___a___ORF RF[1] __a___a___a___a___a____>

1600         1610        1620        1630        1640        1650
   *            *           *           *           *           *
 GCC TCG CTC CTG GCC GCG CCC CCG GTG GCC CCG GCC GAG GCC CCG CAC CTG GTG CAT
 Ala Ser Leu Leu Ala Ala Pro Pro Val Ala Pro Ala Glu Ala Pro His Leu Val His>
 ___a___a___a___a___a___a___a____ORF RF[1] _a___a___a___a___a___a___a___a___>

1660        1670        1680        1690        1700        1710
          *           *           *           *           *           *
 GTG GAC GCG GCC CGC GCG CTG TGG CCC CTG CGG CGC TTC TGG AGG AGC ACA GGC TTC
 Val Asp Ala Ala Arg Ala Leu Trp Pro Leu Arg Arg Phe Trp Arg Ser Thr Gly Phe>
 ___a___a___a___a___a___a___a____ORF RF[1] _a___a___a___a___a___a___a___a___>

1720        1730        1740        1750        1760        1770
          *           *           *           *           *           *
 TGC CCC CCG CTG CCA CAC AGC CAG GCT GAC CAG TAC GTC CTC AGC TGG GAC CAG CAG
 Cys Pro Pro Leu Pro His Ser Gln Ala Asp Gln Tyr Val Leu Ser Trp Asp Gln Gln>
 ___a___a___a___a___a___a___a____ORF RF[1] _a___a___a___a___a___a___a___a___>

1780        1790        1800        1810        1820
          *           *           *           *           *
 CTC AAC CTC GCC TAT GTG GGC GCC GTC CCT CAC CGC GGC ATC AAG CAG GTC CGG ACC
 Leu Asn Leu Ala Tyr Val Gly Ala Val Pro His Arg Gly Ile Lys Gln Val Arg Thr>
 ___a___a___a___a___a___a___a____ORF RF[1] _a___a___a___a___a___a___a___a___>

1830        1840        1850        1860        1870        1880
   *           *           *           *           *           *
 CAC TGG CTG CTG GAG CTT GTC ACC ACC AGG GGG TCC ACT GGA CGG GGC CTG AGC TAC
 His Trp Leu Leu Glu Leu Val Thr Thr Arg Gly Ser Thr Gly Arg Gly Leu Ser Tyr>
```

FIGURE 1A

```
___a___a___a___a___a___a___a____ORF RF[1] _a___a___a___a___a___a___a___a___>
     1890        1900        1910        1920        1930        1940
      *           *           *           *           *           *
AAC TTC ACC CAC CTG GAC GGG TAC CTG GAC CTT CTC AGG GAG AAC CAG CTC CTC CCA
Asn Phe Thr His Leu Asp Gly Tyr Leu Asp Leu Leu Arg Glu Asn Gln Leu Leu Pro>
___a___a___a___a___a___a___a____ORF RF[1] _a___a___a___a___a___a___a___a___>
     1950        1960        1970        1980        1990
      *           *           *           *           *
GGG TTT GAG CTG ATG GGC AGC GCC TCG GGC CAC TTC ACT GAC TTT GAG GAC AAG CAG
Gly Phe Glu Leu Met Gly Ser Ala Ser Gly His Phe Thr Asp Phe Glu Asp Lys Gln>
___a___a___a___a___a___a___a____ORF RF[1] _a___a___a___a___a___a___a___a___>
2000        2010        2020        2030        2040        2050
 *           *           *           *           *           *
CAG GTG TTT GAG TGG AAG GAC TTG GTC TCC AGC CTG GCC AGG AGA TAC ATC GGT AGG
Gln Val Phe Glu Trp Lys Asp Leu Val Ser Ser Leu Ala Arg Arg Tyr Ile Gly Arg>
___a___a___a___a___a___a___a____ORF RF[1] _a___a___a___a___a___a___a___a___>
     2060        2070        2080        2090        2100        2110
      *           *           *           *           *           *
TAC GGA CTG GCG CAT GTT TCC AAG TGG AAC TTC GAG ACG TGG AAT GAG CCA GAC CAC
Tyr Gly Leu Ala His Val Ser Lys Trp Asn Phe Glu Thr Trp Asn Glu Pro Asp His>
___a___a___a___a___a___a___a____ORF RF[1] _a___a___a___a___a___a___a___a___>
     2120        2130        2140        2150        2160
      *           *           *           *           *
CAC GAC TTT GAC AAC GTC TCC ATG ACC ATG CAA GGC TTC CTG AAC TAC TAC GAT GCC
His Asp Phe Asp Asn Val Ser Met Thr Met Gln Gly Phe Leu Asn Tyr Tyr Asp Ala>
___a___a___a___a___a___a___a____ORF RF[1] _a___a___a___a___a___a___a___a___>
2170        2180        2190        2200        2210        2220
 *           *           *           *           *           *
TGC TCG GAG GGT CTG CGC GCC GCC AGC CCC GCC CTG CGG CTG GGA GGC CCC GGC GAC
Cys Ser Glu Gly Leu Arg Ala Ala Ser Pro Ala Leu Arg Leu Gly Gly Pro Gly Asp>
___a___a___a___a___a___a___a____ORF RF[1] _a___a___a___a___a___a___a___a___>
     2230        2240        2250        2260        2270        2280
      *           *           *           *           *           *
TCC TTC CAC ACC CCA CCG CGA TCC CCG CTG AGC TGG GGC CTC CTG CGC CAC TGC CAC
Ser Phe His Thr Pro Pro Arg Ser Pro Leu Ser Trp Gly Leu Leu Arg His Cys His>
___a___a___a___a___a___a___a____ORF RF[1] _a___a___a___a___a___a___a___a___>
     2290        2300        2310        2320        2330        2340
      *           *           *           *           *           *
GAC GGT ACC AAC TTC TTC ACT GGG GAG GCG GGC GTG CGG CTG GAC TAC ATC TCC CTC
Asp Gly Thr Asn Phe Phe Thr Gly Glu Ala Gly Val Arg Leu Asp Tyr Ile Ser Leu>
___a___a___a___a___a___a___a____ORF RF[1] _a___a___a___a___a___a___a___a___>
     2350        2360        2370        2380        2390
      *           *           *           *           *
CAC AGG AAG GGT GCG CGC AGC TCC ATC TCC ATC CTG GAG CAG GAG AAG GTC GTC GCG
His Arg Lys Gly Ala Arg Ser Ser Ile Ser Ile Leu Glu Gln Glu Lys Val Val Ala>
___a___a___a___a___a___a___a____ORF RF[1] _a___a___a___a___a___a___a___a___>
2400        2410        2420        2430        2440        2450
 *           *           *           *           *           *
CAG CAG ATC CGG CAG CTC TTC CCC AAG TTC GCG GAC ACC CCC ATT TAC AAC GAC GAG
Gln Gln Ile Arg Gln Leu Phe Pro Lys Phe Ala Asp Thr Pro Ile Tyr Asn Asp Glu>
___a___a___a___a___a___a___a____ORF RF[1] _a___a___a___a___a___a___a___a___>
```

FIGURE 1B

```
        2460          2470          2480          2490          2500          2510
          *             *             *             *             *             *
    GCG GAC CCG CTG GTG GGC TGG TCC CTG CCA CAG CCG TGG AGG GCG GAC GTG ACC TAC
    Ala Asp Pro Leu Val Gly Trp Ser Leu Pro Gln Pro Trp Arg Ala Asp Val Thr Tyr>
    ___a___a___a___a___a___a___a____ORF RF[1] _a___a___a___a___a___a___a___a___>

2520          2530          2540          2550          2560
             *             *             *             *             *
    GCG GCC ATG GTG GTG AAG GTC ATC GCG CAG CAT CAG AAC CTG CTA CTG GCC AAC ACC
    Ala Ala Met Val Val Lys Val Ile Ala Gln His Gln Asn Leu Leu Leu Ala Asn Thr>
    ___a___a___a___a___a___a___a____ORF RF[1] _a___a___a___a___a___a___a___a___>

2570          2580          2590          2600          2610          2620
    *             *             *             *             *             *
    ACC TCC GCC TTC CCC TAC GCG CTC CTG AGC AAC GAC AAT GCC TTC CTG AGC TAC CAC
    Thr Ser Ala Phe Pro Tyr Ala Leu Leu Ser Asn Asp Asn Ala Phe Leu Ser Tyr His>
    ___a___a___a___a___a___a___a____ORF RF[1] _a___a___a___a___a___a___a___a___>

2630          2640          2650          2660          2670          2680
             *             *             *             *             *             *
    CCG CAC CCC TTC GCG CAG CGC ACG CTC ACC GCG CGC TTC CAG GTC AAC AAC ACC CGC
    Pro His Pro Phe Ala Gln Arg Thr Leu Thr Ala Arg Phe Gln Val Asn Asn Thr Arg>
    ___a___a___a___a___a___a___a____ORF RF[1] _a___a___a___a___a___a___a___a___>

2690          2700          2710          2720          2730
             *             *             *             *             *
    CCG CCG CAC GTG CAG CTG TTG CGC AAG CCG GTG CTC ACG GCC ATG GCG CTG CTG GCG
    Pro Pro His Val Gln Leu Leu Arg Lys Pro Val Leu Thr Ala Met Gly Leu Leu Ala>
    ___a___a___a___a___a___a___a____ORF RF[1] _a___a___a___a___a___a___a___a___>

2740          2750          2760          2770          2780          2790
    *             *             *             *             *             *
    CTG CTG GAT GAG GAG CAG CTC TGG GCC GAA GTG TCG CAG GCC GGG ACC GTC CTG GAC
    Leu Leu Asp Glu Glu Gln Leu Trp Ala Glu Val Ser Gln Ala Gly Thr Val Leu Asp>
    ___a___a___a___a___a___a___a____ORF RF[1] _a___a___a___a___a___a___a___a___>

2800          2810          2820          2830          2840          2850
             *             *             *             *             *             *
    AGC AAC CAC ACG GTG GGC GTC CTG GCC AGC GCC CAC CGC CCC CAG GGC CCG GCC GAC
    Ser Asn His Thr Val Gly Val Leu Ala Ser Ala His Arg Pro Gln Gly Pro Ala Asp>
    ___a___a___a___a___a___a___a____ORF RF[1] _a___a___a___a___a___a___a___a___>

2860          2870          2880          2890          2900          2910
             *             *             *             *             *             *
    GCC TGG CGC GCC GCG GTG CTG ATC TAC GCG AGC GAC GAC ACC CGC GCC CAC CCC AAC
    Ala Trp Arg Ala Ala Val Leu Ile Tyr Ala Ser Asp Asp Thr Arg Ala His Pro Asn>
    ___a___a___a___a___a___a___a____ORF RF[1] _a___a___a___a___a___a___a___a___>

2920          2930          2940          2950          2960
             *             *             *             *             *
    CGC AGC GTC GCG GTG ACC CTG CGG CTG CGC GGG GTG CCC CCC GGC CCG GGC CTG GTC
    Arg Ser Val Ala Val Thr Leu Arg Leu Arg Gly Val Pro Pro Gly Pro Gly Leu Val>
    ___a___a___a___a___a___a___a____ORF RF[1] _a___a___a___a___a___a___a___a___>

2970          2980          2990          3000          3010          3020
    *             *             *             *             *             *
    TAC GTC ACG CGC TAC CTG GAC AAC GGG CTC TGC AGC CCC GAC GGC GAG TGG CGG CGC
    Tyr Val Thr Arg Tyr Leu Asp Asn Gly Leu Cys Ser Pro Asp Gly Glu Trp Arg Arg>
    ___a___a___a___a___a___a___a____ORF RF[1] _a___a___a___a___a___a___a___a___>

```
CTG GGC CGG CCC GTC TTC CCC ACG GCA GAG CAG TTC CGG CGC ATG CGC GCG GCT GAG
Leu Gly Arg Pro Val Phe Pro Thr Ala Glu Gln Phe Arg Arg Met Arg Ala Ala Glu>
___a___a___a___a___a___a___a___ORF RF[1] _a___a___a___a___a___a___a___a___>
        3090        3100        3110        3120        3130
          *           *           *           *           *           *
GAC CCG GTG GCC GCG GCG CCC CGC CCC TTA CCC GCC GGC GGC CGC CTG ACC CTG CGC
Asp Pro Val Ala Ala Ala Pro Arg Pro Leu Pro Ala Gly Gly Arg Leu Thr Leu Arg>
___a___a___a___a___a___a___a___ORF RF[1] _a___a___a___a___a___a___a___a___>
3140        3150        3160        3170        3180        3190
  *           *           *           *           *           *
CCC GCG CTG CGG CTG CCG TCG CTT TTG CTG GTG CAC GTG TGT GCG CGC CCC GAG AAG
Pro Ala Leu Arg Leu Pro Ser Leu Leu Leu Val His Val Cys Ala Arg Pro Glu Lys>
___a___a___a___a___a___a___a___ORF RF[1] _a___a___a___a___a___a___a___a___>
        3200        3210        3220        3230        3240        3250
          *           *           *           *           *           *
CCG CCC GGG CAG GTC ACG CGG CTC CGC GCC CTG CCC CTG ACC CAA GCG CAG CTG GTT
Pro Pro Gly Gln Val Thr Arg Leu Arg Ala Leu Pro Leu Thr Gln Ala Gln Leu Val>
___a___a___a___a___a___a___a___ORF RF[1] _a___a___a___a___a___a___a___a___>
        3260        3270        3280        3290        3300
          *           *           *           *           *           *
CTG GTC TGG TCG GAT GAA CAC GTG GGC TCC AAG TGC CTG TGG ACA TAC GAG ATC CAG
Leu Val Trp Ser Asp Glu His Val Gly Ser Lys Cys Leu Trp Thr Tyr Glu Ile Gln>
___a___a___a___a___a___a___a___ORF RF[1] _a___a___a___a___a___a___a___a___>
3310        3320        3330        3340        3350        3360
  *           *           *           *           *           *
TTC TCT CAG GAC GGT AAG GCG TAC ACC CCG GTC AGC AGG AAG CCA TCG ACC TTC AAC
Phe Ser Gln Asp Gly Lys Ala Tyr Thr Pro Val Ser Arg Lys Pro Ser Thr Phe Asn>
___a___a___a___a___a___a___a___ORF RF[1] _a___a___a___a___a___a___a___a___>
        3370        3380        3390        3400        3410        3420
          *           *           *           *           *           *
CTC TTT GTG TTC AGC CCA GAC ACA GGT GCT GTC TCT GGC TCC TAC CGA GTT CGA GCC
Leu Phe Val Phe Ser Pro Asp Thr Gly Ala Val Ser Gly Ser Tyr Arg Val Arg Ala>
___a___a___a___a___a___a___a___ORF RF[1] _a___a___a___a___a___a___a___a___>
        3430        3440        3450        3460        3470        3480
          *           *           *           *           *           *
CTG GAC TAC TGG GCC CGA CCA GGC CCC TTC TCG GAC CCT GTG CCG TAC CTG GAG GTC
Leu Asp Tyr Trp Ala Arg Pro Gly Pro Phe Ser Asp Pro Val Pro Tyr Leu Glu Val>
___a___a___a___a___a___a___a___ORF RF[1] _a___a___a___a___a___a___a___a___>
        3490        3500        3510        3520        3530        3540
          *           *           *           *           *           *
CCT GTG CCA AGA GGG CCC CCA TCC CCG GGC AAT CCA TGAG CCTGTGCTGA GCCCCAGTGG
Pro Val Pro Arg Gly Pro Pro Ser Pro Gly Asn Pro>
___a___a___a___a__ORF RF[1] ___a___a___a___a___>
        3550        3560        3570        3580        3590        3600        3610
          *           *           *           *           *           *           *
GTTGCACCTC CACCGGCAGT CAGCGAGCTG GGGCTGCACT GTGCCCATGC TGCCCTCCCA TCACCCCCTT
        3620        3630        3640        3650        3660        3670        3680
          *           *           *           *           *           *           *
TGCAATATAT TTTTATATTT TAAAAAAAAA AAAAAAAAAA AAAAAAAAAA AAAAAAAAAA AAAAAAAAAA
        3690        3700        3710        3720        3730        3740        3750
          *           *           *           *           *           *           *
```

FIGURE 1D

```
AAAAAAAAAA AAAAAAAAAG AATTCCTGCA GCCCGGGGGA TCCACTAGTT CTAGAGGGCC CGTTTAAACC
    3760       3770       3780       3790       3800       3810       3820
     * *        * *        * *        * *        * *        * *        * *
CGCTGATCAG CCTCGACTGT GCCTTCTAGT TGCCAGCCAT CTGTTGTTTG CCCCTCCCCC GTGCCTTCCT
    3830       3840       3850       3860       3870       3880       3890
     * *        * *        * *        * *        * *        * *        * *
TGACCCTGGA AGGTGCCACT CCCACTGTCC TTTCCTAATA AAATGAGGAA ATTGCATCGC ATTGTCTGAG
    3900       3910       3920       3930       3940       3950       3960
     * *        * *        * *        * *        * *        * *        * *
TAGGTGTCAT TCTATTCTGG GGGGTGGGGT GGGGCAGGAC AGCAAGGGGG AGGATTGGGA AGACAATAGC
    3970       3980       3990       4000       4010       4020       4030
     * *        * *        * *        * *        * *        * *        * *
AGGCATGCTG GGGATGCGGT GGGCTCTATG GCTTCTGAGG CGGAAAGAAC CAGCTGGGGC TCGAGAGCTT
    4040       4050       4060       4070       4080       4090       4100
     * *        * *        * *        * *        * *        * *        * *
GGCGTAATCA TGGTCATAGC TGTTTCCTGT GTGAAATTGT TATCCGCTCA CAATTCCACA CAACATACGA
    4110       4120       4130       4140       4150       4160       4170
     * *        * *        * *        * *        * *        * *        * *
GCCGGAAGCA TAAAGTGTAA AGCCTGGGGT GCCTAATGAG TGAGCTAACT CACATTAATT GCGTTGCGCT
    4180       4190       4200       4210       4220       4230       4240
     * *        * *        * *        * *        * *        * *        * *
CACTGCCCGC TTTCCAGTCG GGAAACCTGT CGTGCCAGCT GCATTAATGA ATCGGCCAAC GCGCGGGGAG
    4250       4260       4270       4280       4290       4300       4310
     * *        * *        * *        * *        * *        * *        * *
AGGCGGTTTG CGTATTGGGC GCTCTTCCGC TTCCTCGCTC ACTGACTCGC TGCGCTCGGT CGTTCGGCTG
    4320       4330       4340       4350       4360       4370       4380
     * *        * *        * *        * *        * *        * *        * *
CGGCGAGCGG TATCAGCTCA CTCAAAGGCG GTAATACGGT TATCCACAGA ATCAGGGGAT AACGCAGGAA
    4390       4400       4410       4420       4430       4440       4450
     * *        * *        * *        * *        * *        * *        * *
AGAACATGTG AGCAAAAGGC CAGCAAAAGG CCAGGAACCG TAAAAAGGCC GCGTTGCTGG CGTTTTTCCA
    4460       4470       4480       4490       4500       4510       4520
     * *        * *        * *        * *        * *        * *        * *
TAGGCTCCGC CCCCCTGACG AGCATCACAA AAATCGACGC TCAAGTCAGA GGTGGCGAAA CCCGACAGGA
    4530       4540       4550       4560       4570       4580       4590
     * *        * *        * *        * *        * *        * *        * *
CTATAAAGAT ACCAGGCGTT TCCCCCTGGA AGCTCCCTCG TGCGCTCTCC TGTTCCGACC CTGCCGCTTA
    4600       4610       4620       4630       4640       4650       4660
     * *        * *        * *        * *        * *        * *        * *
CCGGATACCT GTCCGCCTTT CTCCCTTCGG GAAGCGTGGC GCTTTCTCAA TGCTCACGCT GTAGGTATCT
    4670       4680       4690       4700       4710       4720       4730
     * *        * *        * *        * *        * *        * *        * *
CAGTTCGGTG TAGGTCGTTC GCTCCAAGCT GGGCTGTGTG CACGAACCCC CCGTTCAGCC CGACCGCTGC
    4740       4750       4760       4770       4780       4790       4800
     * *        * *        * *        * *        * *        * *        * *
GCCTTATCCG GTAACTATCG TCTTGAGTCC AACCCGGTAA GACACGACTT ATCGCCACTG GCAGCAGCCA
```

FIGURE 1E

```
       4810        4820        4830        4840        4850        4860        4870
         *           *           *           *           *           *           *
    CTGGTAACAG  GATTAGCAGA  GCGAGGTATG  TAGGCGGTGC  TACAGAGTTC  TTGAAGTGGT  GGCCTAACTA 4880        4890        4900        4910        4920        4930        4940
         *           *           *           *           *           *           *
    CGGCTACACT  AGAAGGACAG  TATTTGGTAT  CTGCGCTCTG  CTGAAGCCAG  TTACCTTCGG  AAAAAGAGTT 4950        4960        4970        4980        4990        5000        5010
         *           *           *           *           *           *           *
    GGTAGCTCTT  GATCCGGCAA  ACAAACCACC  GCTGGTAGCG  GTGGTTTTTT  TGTTTGCAAG  CAGCAGATTA 5020        5030        5040        5050        5060        5070        5080
         *           *           *           *           *           *           *
    CGCGCAGAAA  AAAAGGATCT  CAAGAAGATC  CTTTGATCTT  TTCTACGGGG  TCTGACCCTC  AGTGGAACGA 5090        5100        5110        5120        5130        5140        5150
         *           *           *           *           *           *           *
    AAACTCACGT  TAAGGGATTT  TGGTCATGAG  ATTATCAAAA  AGGATCTTCA  CCTAGATCCT  TTTAAATTAA 5160        5170        5180        5190        5200        5210        5220
         *           *           *           *           *           *           *
    AAATGAAGTT  TTAAATCAAT  CTAAAGTATA  TATGAGTAAA  CTTGGTCTGA  CAGTTACCAA  TGCTTAATCA 5230        5240        5250        5260        5270        5280        5290
         *           *           *           *           *           *           *
    GTGAGGCACC  TATCTCAGCG  ATCTGTCTAT  TTCGTTCATC  CATAGTTGCC  TGACTCCCCG  TCGTGTAGAT 5300        5310        5320        5330        5340        5350        5360
         *           *           *           *           *           *           *
    AACTACGATA  CGGGAGGGCT  TACCATCTGG  CCCCAGTGCT  GCAATGATAC  CGCGAGACCC  ACGCTCACCG 5370        5380        5390        5400        5410        5420        5430
         *           *           *           *           *           *           *
    GCTCCAGATT  TATCAGCAAT  AAACCAGCCA  GCCGGAAGGG  CCGAGCGCAG  AAGTGGTCCT  GCAACTTTAT 5440        5450        5460        5470        5480        5490        5500
         *           *           *           *           *           *           *
    CCGCCTCCAT  CCAGTCTATT  AATTGTTGCC  GGGAAGCTAG  AGTAAGTAGT  TCGCCAGTTA  ATAGTTTGCG 5510        5520        5530        5540        5550        5560        5570
         *           *           *           *           *           *           *
    CAACGTTGTT  GCCATTGCTA  CAGGCATCGT  GGTGTCACGC  TCGTCGTTTG  GTATGGCTTC  ATTCAGCTCC 5580        5590        5600        5610        5620        5630        5640
         *           *           *           *           *           *           *
    GGTTCCCAAC  GATCAAGGCG  AGTTACATGA  TCCCCCATGT  TGTGCAAAAA  AGCGGTTAGC  TCCTTCGGTC 5650        5660        5670        5680        5690        5700        5710
         *           *           *           *           *           *           *
    CTCCGATCGT  TGTCAGAAGT  AAGTTGGCCG  CAGTGTTATC  ACTCATGGTT  ATGGCAGCAC  TGCATAATTC 5720        5730        5740        5750        5760        5770        5780
         *           *           *           *           *           *           *
    TCTTACTGTC  ATGCCATCCG  TAAGATGCTT  TTCTGTGACT  GGTGAGTACT  CAACCAAGTC  ATTCTGAGAA 5790        5800        5810        5820        5830        5840        5850
         *           *           *           *           *           *           *
    TAGTGTATGC  GGCGACCGAG  TTGCTCTTGC  CCGGCGTCAA  TACGGGATAA  TACCGCGCCA  CATAGCAGAA 5860        5870        5880        5890        5900        5910        5920
         *           *           *           *           *           *           *
```

FIGURE 1F

```
CTTTAAAAGT GCTCATCATT GGAAAACGTT CTTCGGGGCG AAAACTCTCA AGGATCTTAC CGCTGTTGAG
    5930       5940       5950       5960       5970       5980       5990
     *  *       *  *       *  *       *  *       *  *       *  *       *  *
ATCCAGTTCG ATGTAACCCA CTCGTGCACC CAACTGATCT TCAGCATCTT TTACTTTCAC CAGCGTTTCT
    6000       6010       6020       6030       6040       6050       6060
     *  *       *  *       *  *       *  *       *  *       *  *       *  *
GGGTGAGCAA AAACAGGAAG GCAAAATGCC GCAAAAAAGG GAATAAGGGC GACACGGAAA TGTTGAATAC
    6070       6080       6090       6100       6110       6120       6130
     *  *       *  *       *  *       *  *       *  *       *  *       *  *
TCATACTCTT CCTTTTTCAA TATTATTGAA GCATTTATCA GGGTTATTGT CTCATGAGCG GATACATATT
    6140       6150       6160       6170       6180       6190       6200
     *  *       *  *       *  *       *  *       *  *       *  *       *  *
TGAATGTATT TAGAAAAATA AACAAATAGG GGTTCCGCGC ACATTTCCCC GAAAAGTGCC ACCTGACGTC
```

FIGURE 1G

RECOMBINANT α-L-IDURONIDASE, METHODS FOR PRODUCING AND PURIFYING THE SAME AND METHODS FOR TREATING DISEASES CAUSED BY DEFICIENCIES THEREOF

FIELD OF THE INVENTION

The present invention is in the field of molecular biology, enzymology, biochemistry and clinical medicine. In particular, the present invention provides a recombinant α-L-iduronidase, methods to produce and purify this enzyme as well as methods to treat certain genetic disorders including α-L-iduronidase deficiency and mucopolysaccharidosis I (MPS I).

BACKGROUND OF THE INVENTION

Carbohydrates play a number of important roles in the functioning of living organisms. In addition to their metabolic roles, carbohydrates are structural components of the human body covalently attached to numerous other entities such as proteins and lipids (called glycoconjugates). For example, human connective tissues and cell membranes comprise proteins, carbohydrates and a proteoglycan matrix. The carbohydrate portion of this proteoglycan matrix provides important properties to the body's structure.

A genetic deficiency of the carbohydrate-cleaving, lysosomal enzyme α-L-iduronidase causes a lysosomal storage disorder known as mucopolysaccharidosis I (MPS I) (Neufeld, E. F., and Muenzer, J. (1989). The mucopolysaccharidoses in "The Metabolic Basis of Inherited Disease" (Scriver, C. R., Beaudet, A. L., Sly, W. S., and Valle, D., Eds.), pp. 1565–1587, McGraw-Hill, New York). In a severe form, MPS I is commonly known as Hurler syndrome and is associated with multiple problems such as mental retardation, clouding of the cornea, coarsened facial features, cardiac disease, respiratory disease, liver and spleen enlargement, hernias, and joint stiffness. Patients suffering, from Hurler syndrome usually die before age 10. In an intermediate form known as Hurler-Scheie syndrome, mental function is generally not severely affected, but physical problems may lead to death by the teens or twenties. Scheie syndrome is the mildest form of MPS I. It is compatible with a normal life span, but joint stiffness, corneal clouding and heart valve disease cause significant problems.

The frequency of MPS I is estimated to be 1:100,000 according to a British Columbia survey of all newborns (Lowry et al., *Human Genetics* 85:389–390 (1990)) and 1:70,000 according to an Irish study (Nelson, *Human Genetics* 101:355–358 (1990)). There appears to be no ethnic predilection for this disease. It is likely that worldwide the disease is underdiagnosed either because the patient dies of a complication before the diagnosis is made or because the milder forms of the syndrome may be mistaken for arthritis or missed entirely. Effective newborn screening for MPS I would likely find some previously undetected patients.

Except for bone marrow transplantation, there are no significant therapies available for MPS I. Bone marrow transplants can be effective in treating some of the symptoms of the disorder but have high morbidity and mortality in MPS I and often are not available to patients because of a lack of suitable donors. An alternative therapy available to all affected patients would provide an important breakthrough in treating an d managing this disease.

Enzyme replacement therapy has long been considered a potential therapy for MPS I following the discovery that α-L-iduronidase can correct the enzymatic defect in Hurler cells in culture. In this corrective process, the enzyme containing a mannose-6-phosphate residue is taken up into cells through receptor-mediated endocytosis and transported to the lysosomes where it clears the stored substrates, heparan sulfate and dermatan sulfate. Application of this therapy to humans has previously not been possible due to inadequate sources of α-L-iduronidase in tissues. The enzyme replacement concept was first effectively applied to Gaucher patients in a modified placental glucocerebrosidase. The delivery and effective uptake of glucocerebrosidase in Gaucher patients demonstrated that an enzyme could be taken up in vivo in sufficient quantities to provide effective therapy.

For α-L-iduronidase enzyme therapy in MPS I, a recombinant source of enzyme has been needed in order to obtain therapeutically sufficient supplies of the enzyme. The mammalian enzyme was cloned in 1990 (Stoltzfus et al., *J. Biol. Chem.* 267:6570–6575 (1992), and the human enzyme was cloned in 1991 (Moskowitz et al., *FASEB J* 6:A77 (1992)).

DESCRIPTION OF THE FIGURES

FIG. 1 (SEQ ID NO:1 & SEQ ID NO:2) represents the nucleotide and deduced amino acid sequences of cDNA encoding α-L -iduronidase. Nucleotides 1 through 6200 are provided. Amino acids are provided starting with the first methionine in the open reading frame.

BRIEF SUMMARY OF THE INVENTION

Figure 2:
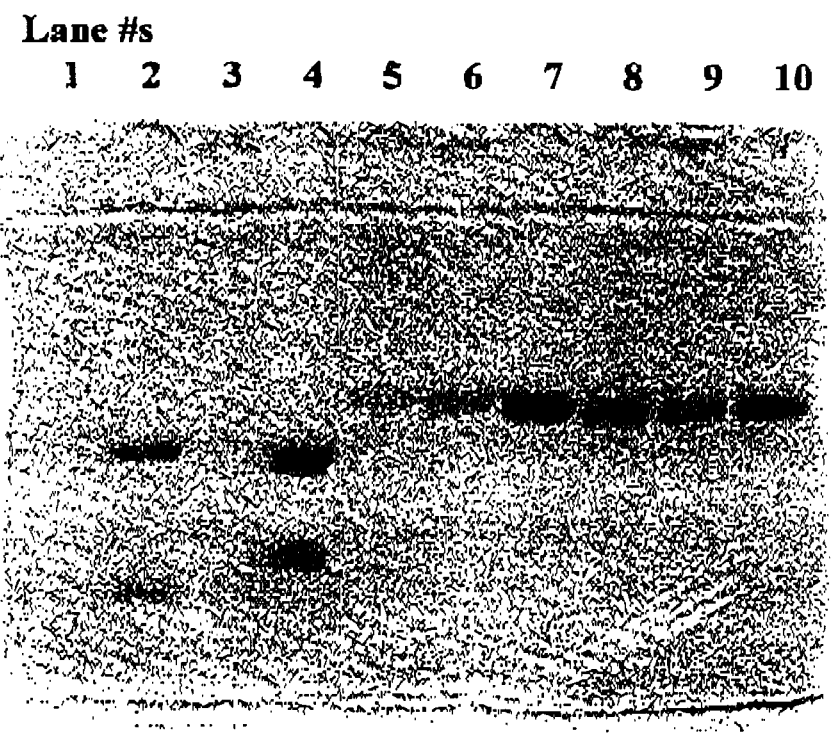
FIG. 2 represents the results from an SDS-PAGE run of eluate obtained according to the procedure set forth in Example 1. Lane 1 is blank. Lane 2 contained high molecular weight standards. Lane 3 is a blank. Lane 4 contained bovine serum albumin in a concentration of 50 µg. Lanes 5 through 10 represent eluate containing recombinantly produced human α-L-iduronidase in amounts of 1 µg, 2 µg, 5 µg, 5 µg, 5 µg and 5 µg, respectively.

In one aspect, the present invention features a method to produce α-L-iduronidase in amounts which enable using the enzyme therapeutically. In a broad embodiment, the method comprises the step of transfecting a cDNA encoding for all or a part of an α-L-iduronidase into a cell suitable for the expression thereof. In some embodiments, a cDNA encoding for a complete α-L-iduronidase is used, preferably a human α-L-iduronidase. However, in other embodiments, a cDNA encoding for a biologically active fragment or mutant thereof may be used. Specifically, one or more amino acid substitutions may be made while preserving or enhancing the biological activity of the enzyme. In other preferred embodiments, an expression vector is used to transfer the cDNA into a suitable cell or cell line for expression thereof. In one particularly preferred embodiment, the cDNA is transfected into a Chinese hamster ovary cell to create cell line 2.131. In yet other preferred embodiments, the production procedure features one or more of the following characteristics which have demonstrated particularly high production levels: (a) the pH of the cell growth culture may be lowered to about 6.5 to 7.0, preferably to about 6.7–6.8 during the production process, (b) about ⅔ to ¾ of the medium may be changed approximately every 12 hours, (c) oxygen saturation may be optimized at about 80% using intermittent pure oxygen sparging, (d) microcarriers with about 10% serum initially may be used to produce cell mass followed by a rapid washout shift to protein-free medium for production, (e) a protein-free or low protein medium such as a JRH Biosciences PF-CHO product may be consisting of glutamate, aspartate, glycine, ribonucleosides and deoxyribonucleosides, (f) a perfusion wand such as a Bellco perfusion wand may be used in a frequent batch-feed process rather than a standard intended perfusion process, and (g) a mild sodium-butyrate induction process may be used to induce increased α-L-iduronidase expression.

In a second aspect, the present invention provides a transfected cell line which features the ability to produce α-L-iduronidase in amounts which enable using the enzyme therapeutically. In preferred embodiments, the present invention features a recombinant Chinese hamster ovary cell line such as the 2.131 cell line that stably and reliably produces amounts of α-L-iduronidase which enable using the enzyme therapeutically. In some preferred embodiments, the cell line may contain at least about 10 copies of a an expression construct. In even more preferred embodiments, the cell line expresses recombinant α-L-iduronidase in amounts of at least about 20–40 micrograms per $10^7$ cells per day.

In a third aspect, the present invention provides novel vectors suitable to produce α-L-iduronidase in amounts which enable using the enzyme therapeutically. In preferred embodiments, the present invention features an expression vector comprising a cytomegalovirus promoter/enhancer element, a 5' intron consisting of a murine Ca intron, a cDNA encoding all or a fragment or mutant of an α-L-iduronidase, and a 3' bovine growth hormone polyadenylation site. Also, preferably the cDNA encoding all or a fragment or mutant of an α-L-iduronidase is about 2.2 kb in length. This expression vector may be transfected at, for example, a 50 to 1 ratio with any appropriate common selection vector such as, for example, pSV2NEO, to enhance multiple copy insertions. Alternatively, gene amplification may be used to induce multiple copy insertions.

In a fourth aspect, the present invention provides novel α-L-iduronidase produced in accordance with the methods of the present invention and thereby present in amounts which enable using the enzyme therapeutically. The specific activity of the α-L-iduronidase according to the present invention is in excess of 200,000 units per milligram protein. Preferably, it is in excess of about 240,000 units per milligram protein. The molecular weight of the α-L-iduronidase of the present invention is about 82,000 daltons, about 70,000 daltons being amino acid and about 12,000 daltons being carbohydrates.

In a fifth aspect, the present invention features a novel method to purify α-L-iduronidase. According to a first embodiment, a cell mass may be grown in about 10% serum containing medium followed by a switch to a modified protein-free production medium without any significant adaptation to produce a high specific activity starting material for purification. Preferably, a concentration/diafiltration scheme is employed that allows for the removal of exogenous materials that may be required for recombinant production of the same such as, for example, Pluronics F-68, a commonly used surfactant for protecting cells from sparging damage. Such exogenous materials should normally be separated from the crude bulk to prevent fouling of the columns. In another preferred embodiment, a first column load is acidified to minimize the competitive inhibition effect of uronic acids found in protein-free medium formulations. In other preferred embodiments, a heparin, phenyl and sizing column purification scheme is used to produce pure enzyme using automatable steps and validatable media. In other preferred embodiments, the heparin and phenyl column steps are used to eliminate less desirable α-L-iduronidase that is nicked or degraded. In yet other preferred embodiments, a three step column chromatography may be used to purify the enzyme. Such a three step column chromatography may include using a blue sepharose FF, a Cu++ chelating sepharose chromatography and a phenyl sepharose HP chromatography. In another preferred embodiment, an acid pH treatment step is used to inactivate potential viruses without harming the enzyme.

In a sixth aspect, the present invention features novel methods of treating diseases caused all or in part by a deficiency in α-L-iduronidase. In one embodiment, this method features administering a recombinant α-L-iduronidase or a biologically active fragment or mutant thereof alone or in combination with a pharmaceutically suitable carrier. In other embodiments, this method features transferring a nucleic acid encoding all or a part of an α-L-iduronidase into one or more host cells in vivo. Preferred embodiments include optimizing the dosage to the needs of the organism to be treated, preferably mammals or humans, to effectively ameliorate the disease symptoms. In preferred embodiments, the disease is mucopolysaccharidosis I (MPS I), Hurler syndrome, Hurler-Scheie syndrome or Scheie syndrome.

In a seventh aspect, the present invention features novel pharmaceutical compositions comprising α-L-iduronidase useful for treating a disease caused all or in part by a deficiency in α-L-iduronidase. Such compositions may be suitable for administration in a number of ways such as parenteral, topical, intranasal, inhalation or oral administration. Within the scope of this aspect are embodiments featuring nucleic acid sequences encoding all or a part of an α-L-iduronidase which may be administered in vivo into cells affected with an α-L-iduronidase deficiency.

DETAILED DESCRIPTION OF THE INVENTION

In one aspect, the present invention features a method to produce α-L-iduronidase in amounts which enable using the enzyme therapeutically. In general, the method features transforming a suitable cell line with the cDNA encoding for all of α-L-iduronidase or a biologically active fragment or mutant thereof. Those of skill in the art may prepare expression constructs other than those expressly described herein for optimal production of α-L-iduronidase in suitable cell lines transfected therewith. Moreover, skilled artisans may easily design fragments of cDNA encoding biologically active fragments and mutants of the naturally occurring α-L-iduronidase which possess the same or similar biological activity to the naturally occurring full-length enzyme.

To create a recombinant source for α-L-iduronidase, a large series of expression vectors may be constructed and tested for expression of a α-L-iduronidase cDNA. Based on transient transfection experiments as well as stable transfections, an expression construct may be identified that provides particularly high level expression. In one embodiment of the present invention, a Chinese hamster cell line 2.131 developed by transfection of the α-L-iduronidase expression construct and selection for a high expression clone provides particularly high level expression. Such a Chinese hamster cell line according to this embodiment of the present invention may secrete about 5,000 to 7,000 fold more α-L-iduronidase than normal. The α-L-iduronidase produced thereby may be properly processed, taken up into cells with high affinity and is corrective for α-L-iduronidase deficient cells such as those from patients suffering from Hurler's Syndrome.

The method for producing α-L-iduronidase in amounts that enable using the enzyme therapeutically features a production process specifically designed to produce the enzyme in high quantities. According to preferred embodiments of such a process, microcarriers are used as a low cost scalable surface on which to grow adherent cells. In especially preferred embodiments, such microcarriers are microporous.

According to other preferred embodiments of the method for producing α-L-iduronidase according to the present invention, a culture system is optimized. In a first embodiment, the culture pH is lowered to about 6.5 to 7.0, preferably to about 6.7–6.8 during the production process. One advantage of such a pH is to enhance accumulation of lysosomal enzymes that are more stable at acidic pH. In a second embodiment, about ⅔ to ¾ of the medium is changed approximately every 12 hours. One advantage of this procedure is to enhance the secretion rate of recombinant α-L-iduronidase and capture more active enzyme. In a third embodiment, oxygen saturation is optimized at about 80% using intermittent pure oxygen sparging rather than continuous sparging. In a fourth embodiment, cytodex 2 microcarriers with about 10% serum initially are used to produce a cell mass followed by a rapid washout shift to a protein-free medium for production. In a fifth embodiment, a growth medium such as a JRH Biosciences PF-CHO product may be optimized to include supplemental amounts of one or more ingredients selected from the group consisting of glutamate, aspartate, glycine, ribonucleosides and deoxyribonucleosides. In a sixth embodiment, a perfusion wand such as a Bellco perfusion wand may be used in a frequent batch-feed process rather than a standard intended perfusion process. In a seventh embodiment, a mild sodium butyrate induction process may be used to induce increased α-L-iduronidase expression without a substantial effect on the carbohydrate processing and cellular uptake of the enzyme. Such an induction process may provide about a two-fold increase in production without significantly altering post-translational processing.

Particularly preferred embodiments of the method for producing α-L-iduronidase according to the present invention feature one, more than one or all of the optimizations described herein. The production method of the present invention may therefore provide a production culture process having the following features:

1. A microcarrier based culture using Cytodex 2 beads or an equivalent thereof is preferably used in large scale culture flasks with overhead wand stirring using a Bellco perfusion wand or an equivalent thereof. Attachment to these beads may be achieved by culture in a 10% fetal bovine serum in DME/F12 1:1 medium modified with ingredients including ribonucleosides, deoxyribonucleosides, pyruvate, non-essential amino acids, and HEPES-and at a pH of about 6.7–6.9. After about 3 days in this medium, a washout procedure is begun in which protein-free medium replaces approximately ⅔ of the medium approximately every 12 hours for a total of about 3–4 washes. Subsequently and throughout the entire remaining culture period, the cells are cultivated in protein-free medium.

2. The culture conditions are preferably maintained at a dissolved oxygen of 80% of air saturation at a pH of about 6.7 and at a temperature of about 37° C. This may be achieved using a control tower, service unit and appropriate probes such as those produced by Wheaton. However, skilled artisans will readily appreciate that this can easily be achieved by equivalent control systems produced by other manufacturers. An air saturation of about 80% results in improved α-L-iduronidase secretion over 40% and 60% air saturation. However 90% air saturation does not provide significantly enhanced secretion over 80% air saturation. The dissolved oxygen may be supplied by intermittent pure oxygen sparging using a 5 micron stainless steel sparger or equivalent thereof. A pH of about 6.7 is optimal for the accumulation of the α-L-iduronidase enzyme. The enzyme is particularly unstable at pH's above about 7.0. Below a pH of about 6.7, the secretion rate may decrease, particularly below a pH of about 6.5. The culture is therefore maintained optimally between a pH of about 6.6 to 6.8.

3. The production culture medium may be a modified form of the commercially available proprietary medium from JRH Biosciences called Excell PF CHO. This medium supports levels of secretion equivalent to that of serum using a cell line such as the 2.131 cell line. It may be preferably modified to include an acidic pH of about 6.7 (+/−0.1), and it may be buffered with HEPES at 7.5 mM. The medium may contain 0.05 to 0.1% of Pluronics F-68 (BASF), a non-ionic surfactant or an equivalent thereof which features the advantage of protecting cells from shear forces associated with sparging. The medium may further contain a proprietary supplement that proves to be important in increasing the productivity of the medium over other protein-free mediums that are presently available. Those skilled in the art will readily understand that the choice of culture medium may be optimized continually according to particular commercial embodiments available at particular points in time. Such changes encompass no more than routine experimentation and are intended to be within the scope of the present invention.

4. The production medium may be analyzed using an amino acid analyzer comparing spent medium with starting medium. Such analyses have demonstrated that the 2.131 cell line depletes a standard PF CHO medium of glycine, glutamate and aspartate to a level of around 10% of the starting concentration. Supplementation of these amino acids to higher levels may result in enhanced culture density and productivity that may lead to a 2–3 fold higher production than at baseline. Skilled artisans will appreciate that other cell lines within the scope of the present invention may be equally useful for producing α-L-iduronidase according to the present method. Hence, more or less supplemental nutrients may be required to optimize the medium. Such optimizations are intended to be within the scope of the present invention and may be practiced without undue experimentation.

5. The medium may be supplemented with ribonucleosides and deoxyribonucleosides to support the dihydrofolate reductase deficient cell line 2.131. Skilled artisans will appreciate that other cell lines within the scope of the present invention may be equally useful for producing α-L-iduronidase according to the present method. Hence, more or less ribonucleosides and deoxyribonucleosides may be required to optimize the medium. Such optimizations are intended within the scope of the present invention and may be practiced without undue experimentation.

6. After reaching confluence at about 3–4 days of culture, approximately ⅔ of the medium may be changed out approximately every 12 hours. The change out of medium may be accomplished using, for instance, a Bellco perfusion wand which is a stirring device with a hollow center and screen filter at its tip. By pumping out medium through the hollow interior of the wand through the 40 micron screen. The microcarriers with the 2.131 cell mass are separated from supernatant containing the enzyme.

7. The rapid and frequent turnover of the medium has been shown by productivity studies to result in improved overall collection of enzyme from the cell culture. Less frequent changes result in less total accumulation of enzyme. Studies of the secretion rate of the enzyme during a 12 hour culture cycle demonstrate that the cells are actively secreting enzyme for the majority of the culture period. More frequent changes are unlikely to yield substantially more enzyme. The method of this embodiment has proven to be superior to perfusion culture and far superior to strict batch culture or daily or every other day batch/feed strategies. Using the every approximately 12 hour change, the cells may be maintained in excellent condition with high degrees of viability and a high level of productivity.

8. Production of α-L-iduronidase may be enhanced by the use of sodium butyrate induction of gene expression. Systematic studies of a 2.131 cell line demonstrated that about 2 mM butyrate can be applied and result in about a two-fold or greater induction of enzyme production with minimal effects on carbohydrate processing. Lower levels of butyrate have not been shown to induce as well, and substantially higher levels may result in higher induction but declining affinity of the produced enzyme for cells from patients suffering from α-L-iduronidase deficiency. The results suggest that two-fold or greater induction results in less processing of the carbohydrates and less phosphate addition to the enzyme as well as increasing toxicity. One particularly preferred method uses 2 mM butyrate addition every 48 hours to the culture system. This embodiment results in about a two-fold induction of enzyme production using this method without significant effect on the uptake affinity of the enzyme, (K-uptake of less than 30 U/ml or 2.0 mM). Using embodiments of the present method featuring all of the above modifications and induction, a 15 liter culture system may produce approximately 25 mg per liter of culture per day, or more at peak culturing density.

In a second aspect, the present invention provides a transfected cell line which possesses the unique ability to produce α-L-iduronidase in amounts which enable using the enzyme therapeutically. In preferred embodiments, the present invention features a recombinant Chinese hamster ovary cell line such as the 2.131 cell line that stably and reliably produces amounts of α-L-iduronidase. In preferred embodiments, the cell line may contain at least about 10 copies of an expression construct comprising a CMV promoter, a Ca intron, a human α-L-iduronidase cDNA, and a bovine growth hormone polyadenylation sequence. In even more preferred embodiments, the cell line expresses α-L-iduronidase at amounts of at least about 20–40 micrograms per $10^7$ cells per day in a properly processed,.high uptake form appropriate for enzyme replacement therapy. According, to preferred embodiments of this aspect of the invention, the transfected cell line adapted to produce α-L-iduronidase in amounts which enable using the enzyme therapeutically possesses one or more of the following features:

1. The cell line of preferred embodiments is derived from a parent cell line wherein the cells are passaged in culture until they have acquired a smaller size and more rapid growth rate and until they readily attach to substrates.

2. The cell line of preferred embodiments is transfected with an expression vector containing the cytomegalovirus promoter/enhancer element, a 5' intron consisting of the murine Ca intron between exons 2 and 3, a human cDNA of about 2.2 kb in length, and a 3' bovine growth hormone polyadenylation site. This expression vector may be transfected at, for example, a 50 to 1 ratio with any appropriate common selection vector such as pSV2NEO. The selection vector pSV2NEO in turn confers G418 resistance on successfully transfected cells. In particularly preferred embodiments, a ratio of about 50 to 1 is used since this ratio enhances the acquisition of multiple copy number inserts. According to one embodiment wherein the Chinese hamster ovary cell line 2.131 is provided, there are approximately 10 copies of the expression vector for α-L-iduronidase. Such a cell line has demonstrated the ability to produce large quantities of human α-L-iduronidase (minimum 20 micrograms per 10 million cells per day). Particularly preferred embodiments such as the 2.131 cell line possess the ability to produce properly processed enzyme that contains N-linked oligosaccharides containing high mannose chains modified with phosphate at the 6 position in sufficient quantity to produce an enzyme with high affinity (K-uptake of less than 3 nM).

3. The enzyme produced from the cell lines of the present invention such as a Chinese hamster ovary cell line 2.131 is rapidly assimilated into cells, eliminates glycosaminoglycan storage and has a half-life of about 5 days in cells from patients suffering from α-L-iduronidase deficiency.

4. The cell line of preferred embodiments such as a 2.131 cell line adapts to large scale culture and stably produces human α-L-iduronidase under these conditions. The cells of preferred embodiments are able to grow and secrete α-L-iduronidase at the acid pH of about 6.6 to 6.8 at which enhanced accumulation of α-L-iduronidase can occur.

5. Particularly preferred embodiments of the cell line according to the invention, such as a 2.131 cell line are able to secrete human α-L-iduronidase at levels exceeding 2,000 units per ml (8 micrograms per ml) twice per day using a specially formulated protein-free medium.

In a third aspect, the present invention provides novel vectors suitable to produce α-L-iduronidase in amounts which enable using the enzyme therapeutically. The production of adequate quantities of recombinant α-L-iduronidase is a critical prerequisite for studies on the structure of the enzyme as well as for enzyme replacement therapy. The cell lines according to the present invention permit the production of significant quantities of recombinant α-L-iduronidase that is appropriately processed for uptake. Overexpression in Chinese hamster ovary (CHO) cells has been described for three other lysosomal enzymes, α-galactosidase (Ioannou et al., *J Cell. Biol.* 119:1137–1150 (1992)), iduronate 2-sulfatase (Bielicki et al., *Biochem. J.* 289: 241–246 (1993)), and N-acetylgalactosamine 4-sulfatase (Amson et al., *Biochem. J.* 284:789–794 (1992)), using, a variety of promoters and, in one case, amplification. The present invention features a dihydrofolate reductase-deficient CHO cell line, but according to preferred embodiments of the invention amplification is unnecessary. Additionally, the present invention provides a high level of expression of the human α-L-iduronidase using the CMV immediate early gene promoter/enhancer.

The present invention features in preferred embodiments an expression vector comprising a cytomegalovirus promoter/enhancer element, a 5' intron consisting of the murine Cα intron derived from the murine long chain immunoglobulin Cα gene between exons 2 and 3, a human cDNA of about 2.2 kb in length, and a 3' bovine growth hormone polyadenylation site. This expression vector may be transfected at, for example, a 50 to 1 ratio with any appropriate common selection vector such as, for example, pSV2NEO. The selection vector such as pSV2NEO in turn confers G418 resistance on successfully transfected cells. In particularly preferred embodiments, a ratio of about 50 to 1 expression vector to selection vector is used since this ratio enhances the acquisition of multiple copy number inserts. According to one embodiment wherein the Chinese hamster ovary cell line 2.131 is provided, there are approximately 10 copies of the expression vector for α-L-iduronidase. Such an expression construct has demonstrated the ability to produce large quantities of human α-L-iduronidase (minimum 20 micrograms per 10 million cells per day) in a suitable cell line such as, for example, a Chinese hamster ovary cell line 2.131.

In a fourth aspect, the present invention provides novel α-L-iduronidase produced in accordance with the methods of the present invention and thereby present in amounts that enable using the enzyme therapeutically. The methods of the present invention produce a substantially pure α-L-iduronidase that is properly processed and in high uptake form appropriate for enzyme replacement therapy and that is effective in therapy in vivo.

The specific activity of the α-L-iduronidase according to the present invention is in excess of about 200,000 units per milligram protein. Preferably, it is in excess of about 240,000 units per milligram protein. The molecular weight of the full length α-L-iduronidase of the present invention is about 82,000 daltons comprising about 70,000 daltons of amino acids and 12,000 daltons of carbohydrates. The recombinant enzyme of the present invention is endocytosed even more efficiently than has been previously reported for a partially purified preparation of urinary enzyme. The recombinant enzyme according to the present invention is effective in reducing the accumulation of radioactive S-labeled GAG in α-L-iduronidase-deficient fibroblasts, indicating that it is transported to lysosomes, the site of GAG storage. The remarkably low concentration of α-L-iduronidase needed for such correction (half-maximal correction at 0.7 pM) may be very important for the success of enzyme replacement therapy.

The human cDNA of α-L-iduronidase predicts a protein of 653 amino acids and an expected molecular weight of 70,000 daltons after signal peptide cleavage. Amino acid sequencing reveals alanine 26 at the N-terminus giving an expected protein of 629 amino acids. Human recombinant α-L-iduronidase has a Histidine at position 8 of the mature protein. The predicted protein sequence comprises six potential N-linked oligosaccharide modification sites. All of these may be modified in the recombinant protein. The third and sixth sites have been demonstrated to contain one or more mannose 6-phosphate residues responsible for high affinity uptake into cells. The following peptide corresponds to Amino Acids 26–45 of Human Recombinant α-L-iduronidase With an N-terminus alanine and the following sequence:

ala-glu-ala-pro-his-leu-val-his-val-asp-ala-ala-arg-ala-leu-trp-pro-leu-arg-arg

The overexpression of the α-L-iduronidase of the present invention does not result in generalized secretion of other lysosomal enzymes that are dependent on mannose-6-P targeting. The secreted recombinant α-L-iduronidase is similar to normal secreted enzyme in many respects. Its molecular size, found in various determinations to be 77, 82, 84, and 89 kDa, is comparable to 87 kDa, found for urinary corrective factor (Barton et al., *J. Biol. Chem.* 246: 7773–7779 (1971)), and to 76 kDa and 82 kDa, found for enzyme secreted by cultured human fibroblasts (Myerowitz et al., *J. Biol. Chem.* 256: 3044–3048 (1991); Taylor et al., *Biochem. J* 274:263–268 (1991)). The differences within and between the studies are attributed to imprecision of the measurements. The pattern of intracellular processing of the recombinant enzyme-a slow decrease in molecular size and the eventual appearance of an additional band smaller by 9 kDa is the same as for the human fibroblast enzyme. This faster band arises by proteolytic cleavage of 80 N-terminal amino acids.

In a fifth aspect, the present invention features a novel method to purify α-L-iduronidase. In preferred embodiments, the present invention features a method to purify recombinant α-L-iduronidase that has been optimized to produce a rapid and efficient purification with validatible chromatography resins and easy load, wash and elute operation. The method of purifying α-L-iduronidase of the present invention involves a series of column chromatography steps which allow the high yield purification of enzyme from protein-free production medium.

According to a first embodiment, the cell mass is grown in about 10 % serum containing medium followed by a switch to a modified protein-free production medium without any significant adaptation to produce a high specific activity starting material for purification. In a second embodiment, a concentration/diafiltration scheme is employed that allows for the removal of such exogenous materials as Pluronics F-68 from the crude bulk to prevent fouling of columns. In a third embodiment, a first column load is acidified to minimize the competitive inhibition effect of such compounds as uronic acids found in protein-free medium formulations. In a fourth embodiment, a heparin, phenyl and sizing column purification scheme is used to produce pure enzyme using automatable steps. In a fifth embodiment, the heparin and phenyl column steps are used to eliminate less desirable α-L-iduronidase that is nicked or degraded. In a sixth embodiment, an acid pH treatment step is used to inactivate potential viruses without harming the enzyme. In a seventh embodiment, a 3 step column chromatography process is followed. The first column involves an affinity chromatography step using Blue Sepharose 6 FF. The Blue eluate is then further purified by another affinity chromatography step using $Cu^{++}$ Chelating Sepharose FF. Finally hydrophobic interaction chromatography using Phenyl Sepharose High Performance (HP) is used.

Particularly preferred embodiments of the method for purifying α-L-iduronidase according to the present invention feature more than one or all of the optimizations according to the following particular embodiments. The purification method of the present invention may therefore provide a purified α-L-iduronidase having the characteristics described herein.

1. Concentration/diafiltration: Crude supernatant is processed with a hollow fiber concentrator (A/G Technologies, 30K cutoff) to reduce fluid volume by about 75% and is then diafiltrated with a heparin load buffer (10 mM $NaPO_4$, pH 5.3, NaCl 200 mM). The diafiltration is an important step that eliminates undesirable compounds such as Pluronics F-68 from the supernatant, a surfactant needed in many cell cultures of the present invention that can foul columns. The diafiltration may also partly remove competitor inhibitors that may prevent binding to the heparin column. These inhibitors may be found in PF-CHO medium and are believed to be uronic acids derived from a soybean hydrolysate present in this particular medium.

2. Heparin column: The load may be adjusted to a pH of about 5.0 before loading on Heparin Sepharose CL-6B. Other types of heparin columns such as a heparin FF (Pharmacia) have different linkages and do not bind α-L-iduronidase as efficiently. A lower pH neutralizes uronic acids to some extent which lessens their competitive effect. Without the diafiltration and pH adjustment, heparin columns cannot be run using PF-CHO medium without having substantial enzyme flowthrough. The column may be washed with a pH of about 5.3 buffer and then eluted in 0.6 M NaCl. The narrow range of binding and elution salt concentration leads to an efficient purification step and enzyme that is often greater than 90% pure after one step.

3. Phenyl column: A Phenyl-Sepharose BP (Pharmacia) may be used in the next step. The heparin eluate may be adjusted to about 1.5 M NaCl and loaded on the column. The choice of resin is important as is the salt concentration in ensuring that the enzyme binds completely (no flow through) and yet elutes easily and completely with about 0.15 M NaCl. The eluate obtained is nearly pure α-L-iduronidase.

4. A pH inactivation may be performed to provide a robust step for the removal of potential viruses. The phenyl pool is adjusted to a pH of about 3.3 using Citrate pH 3.0 and held at room temperature for about 4 hours. The enzyme may then be neutralized. Embodiments featuring this step have been shown to eliminate viruses at a minimum of about 5 log units. The step does not substantially inactivate or affect the enzyme activity.

5. The enzyme may then be concentrated and injected onto a Sephacryl S-200 column and the peak of enzyme collected.

Enzyme purified in this manner has been shown to contain mannose-6-phosphate residues of sufficient quantity at positions 3 and 6 of the N-linked sugars to give the enzyme uptake affinity of less than 30 units per ml (less than 2 nM) enzyme. The enzyme is substantially corrective for glycosamino glycan storage disorders and has a half-life inside cells of approximately 5 days.

In a sixth aspect, the present invention features novel methods of treating diseases caused all or in part by a deficiency in α-L-iduronidase. Recombinant α-L-iduronidase provides enzyme replacement therapy in a canine model of MPS 1. This canine model is deficient in α-L-iduronidase due to a genetic mutation and is similar to human MPS 1. Purified, properly processed α-L-iduronidase was administered intravenously to 11 dogs. In those dogs treated with weekly doses of 25,000 to 125,000 units per kg for 3, 6 or 13 months, the enzyme was taken up in a variety of tissues and decreased the lysosomal storage in many tissues. The long term treatment of the disease was associated with clinical improvement in demeanor, joint stiffness, coat and growth. Higher doses of therapy (125,000 units per kg per week) result in better efficacy and including normalization of urinary GAG excretion in addition to more rapid clinical improvement in demeanor, joint stiffness and coat.

Enzyme therapy at even small doses of 25,000 units (0.1 mg/kg/wk) resulted in significant enzyme distribution to some tissues and decreases in GAG storage. If continued for over 1 year, significant clinical effects of the therapy were evident in terms of activity, mobility, growth and overall health. The therapy at this dose did not improve other tissues that are important sites for disease in this entity such as cartilage and brain. Higher doses of 125,000 units (0.5 mg/kg) given 5 times over two weeks demonstrate that improved tissue penetration can be achieved, and a therapeutic effect at the tissue level was accomplished in as little as 2 weeks. Studies at this increased dose are ongoing in two dogs for six months to date. These MPS I dogs are showing significant clinical improvement and substantial decreases in urinary GAG excretion into the normal range. Other than an immune reaction controlled by altered administration techniques, the enzyme therapy has not shown significant clinical or biochemical toxicity. Enzyme therapy at this higher weekly dose is effective at improving, some clinical features of MPS I and decreasing storage without significant toxicity.

In a seventh aspect, the present invention features novel pharmaceutical compositions comprising human α-L-iduronidase useful for treating a deficiency in α-L-iduronidase. The recombinant enzyme may be administered in a number of ways such as parenteral, topical, intranasal, inhalation or oral administration. Another aspect of the invention is to provide for the administration of the enzyme by formulating it with a pharmaceutically-acceptable carrier which may be solid, semi-solid or liquid or an ingestable capsule. Examples of pharmaceutical compositions include tablets, drops such as nasal drops, compositions for topical application such as ointments, jellies, creams and suspensions, aerosols for inhalation, nasal spray, liposomes. Usually the recombinant enzyme comprises between 0.05 and 99% or between 0.5 and 99% by weight of the composition, for example, between 0.5 and 20% for compositions intended for injection and between 0.1 and 50% for compositions intended for oral administration.

To produce pharmaceutical compositions in this form of dosage units for oral application containing a therapeutic enzyme, the enzyme may be mixed with a solid, pulverulent carrier, for example lactose, saccharose, sorbitol, mannitol, a starch such as potato starch, corn starch, amylopectin, laminaria powder or citrus pulp powder, a cellulose derivative or gelatine and also may include lubricants such as magnesium or calcium stearate or a Carbowax or other polyethylene glycol waxes and compressed to form tablets or cores for dragees. If dragees are required, the cores may be coated for example with concentrated sugar solutions which may contain gum arabic, talc and/or titanium dioxide, or alternatively with a film forming agent dissolved in easily volatile organic solvents or mixtures of organic solvents. Dyestuffs can be added to these coatings, for example, to distinguish between different contents of active substance. For the composition of soft gelatine capsules consisting of gelatine and, for example, glycerol as a plasticizer, or similar closed capsules, the active substance may be admixed with a Carbowax® or a suitable oil as e.g., sesame oil, olive oil, or arachis oil. Hard gelatine capsules may contain granulates of the active substance with solid, pulverulent carriers such as lactose, saccharose, sorbitol, mannitol, starches such as potato starch, corn starch or amylopectin, cellulose derivatives or gelatine, and may also include magnesium stearate or stearic acid as lubricants.

Therapeutic enzymes of the subject invention may also be administered parenterally such as by subcutaneous, intramuscular or intravenous injection or by sustained release subcutaneous implant. In subcutaneous, intramuscular and intravenous injection, the therapeutic enzyme (the active ingredient) may be dissolved or dispersed in a liquid carrier vehicle. For parenteral administration, the active material may be suitably admixed with an acceptable vehicle, preferably of the vegetable oil variety such as peanut oil, cottonseed oil and the like. Other parenteral vehicles such as organic compositions using solketal, glycerol, formal, and aqueous parenteral formulations may also be used.

For parenteral application by injection, compositions may comprise an aqueous solution of a water soluble pharmaceutically acceptable salt of the active acids according to the invention, desirably in a concentration of 0.5–10%, and optionally also a stabilizing agent and/or buffer substances in aqueous solution. Dosage units of the solution may advantageously be enclosed in ampules.

When therapeutic enzymes are administered in the form of a subcutaneous implant, the compound is suspended or dissolved in a slowly dispersed material known to those skilled in the art, or administered in a device which slowly releases the active material through the use of a constant driving force such as an osmotic pump. In such cases, administration over an extended period of time is possible.

For topical application, the pharmaceutical compositions are suitably in the form of an ointment, gel, suspension, cream or the like. The amount of active substance may vary, for example, between 0.05–20% by weight of the active substance. Such pharmaceutical compositions for topical application may be prepared in known manner by mixing the active substance with known carrier materials such as isopropanol, glycerol, paraffin, stearyl alcohol, polyethylene glycol, etc. The pharmaceutically acceptable carrier may also include a known chemical absorption promoter. Examples of absorption promoters are, e.g., dimethylacetamide (U.S. Pat. No. 3,472,931), trichloro ethanol or trifluoroethanol (U.S. Pat. No. 3,891,757), certain alcohols and mixtures thereof (British Patent No. 1,001,949). A carrier material for topical application to unbroken skin is also described in the British patent specification No. 1,464,975, which discloses a carrier material consisting of a solvent comprising 40–70% (v/v) isopropanol and 0–60% (v/v) glycerol, the balance, if any, being an inert constituent of a diluent not exceeding 40% of the total volume of solvent.

The dosage at which the therapeutic enzyme containing pharmaceutical compositions are administered may vary within a wide range and will depend on various factors such as, for example, the severity of the disease, the age of the patient, etc., and may have to be individually adjusted. As a possible range for the amount of therapeutic enzyme which may be administered per day be mentioned from about 0.1 mg to about 2000 mg or from about 1 mg to about 2000 mg.

The pharmaceutical compositions containing the therapeutic enzyme may suitably be formulated so that they provide doses within these ranges either as single dosage units or as multiple dosage units. In addition to containing a therapeutic enzyme (or therapeutic enzymes), the subject formulations may contain one or more substrates or cofactors for the reaction catalyzed by the therapeutic enzyme in the compositions. Therapeutic enzyme containing compositions may also contain more than one therapeutic enzyme.

The recombinant enzyme employed in the subject methods and compositions may also be administered by means of transforming patient cells with nucleic acids encoding the recombinant α-L-iduronidase. The nucleic acid sequence so encoding may be incorporated into a vector for transformation into cells of the subject to be treated. Preferred embodiments of such vectors are described herein. The vector may be designed so as to integrate into the chromosomes of the subject, e.g., retroviral vectors, or to replicate autonomously in the host cells. Vectors containing encoding α-L-iduronidase nucleotide sequences may be designed so as to provide for continuous or regulated expression of the enzyme. Additionally, the genetic vector encoding the enzyme may be designed so as to stably integrate into the cell genome or to only be present transiently. The general methodology of conventional genetic therapy may be applied to polynucleotide sequences encoding α-L-iduronidase. Reviews of conventional genetic therapy techniques can be found in Friedman, *Science* 244:1275–1281 (1989); Ledley, J. *Inherit. Metab. Dis.* 13:587–616 (1990); and Tososhev et al., *Curr Opinions Biotech.* 1:55–61 (1990).

A particularly preferred method of administering the recombinant enzyme is intravenously. A particularly preferred composition comprises recombinant α-L-iduronidase, normal saline, phosphate buffer to maintain the pH at about 5.8 and human albumin. These ingredients may be provided in the following amounts:

| | |
|---|---|
| α-L-iduronidase | 0.05–0.2 mg/mL or 12,500–50,000 units per mL |
| Sodium chloride solution | 150 mM in an IV bag, 50–250 cc total volume |
| Sodium phoshate buffer | 10–50 mM, pH 5.8 |
| Human albumin | 1 mg/mL |

The invention having been described, the following examples are offered to illustrate the subject invention by way of illustration, not by way of limitation.

EXAMPLE 1

Producing Recombinant Iduronidase

Standard techniques such as those described by Sambrook et al. (1987) "Molecular Cloning: A Laboratory Manual", $2^{nd}$ ed., Cold Spring Harbor Laboratory, Cold Spring Harbor, N.Y. may be used to clone cDNA encoding human α-L-iduronidase. The human α-L-iduronidase cDNA previously cloned was subcloned into PRCCMV (InVitrogen) as a HindIII-XbaI fragment from a bluescript KS subclone. An intron cassette derived from the murine immunoglobulin Cot intron between exons 2 and 3 was constructed using PCR amplification of bases 788–1372 (Tucker et al., *Proc. Natl. Acad. Sci. USA* 78: 7684–7688 (1991) of clone pRIRI4.5 (Kakkis et al., *Nucleic Acids Res.* 16:7796 (1988)). The cassette included 136 bp of the 3' end of exon 2 and 242 bp of the 5' end of exon 3, which would remain in the properly spliced cDNA. No ATG sequences are present in the coding, region of the intron cassette. The intron cassette was cloned into the HindIII site 5' of the α-L-iduronidase cDNA. The neo gene was deleted by digestion with XhoI followed by recircularizing the vector to make pCMVhIdu.

One vial of the master cell bank is thawed and placed in three T150 flasks in DME/F12 plus supplements plus 10% FBS and 500 11 g/ml G418. After 3–4 days, the cells are passaged using trypsin-EDTA to 6 high capacity roller bottles in the same medium. The innoculum of $2\times10^9$ cells is added to a Wheaton microcarrier flask containing 60 grams of Cytodex 2 microcarriers, and DME/F12 plus supplements, 10% FBS and 500 11 g/ml of G418 at a final volume of 13 liters. The flask is stirred by a Belico overhead drive with a Perfusion wand stirrer. The culture is monitored by temperature, DO and pH probes and controlled using the Wheaton mini-pilot plant control system with a PC interface (BioPro software). The parameters are controlled at the set points, 37° C., 80% air saturation, and pH 6.7, using a heating-blanket, oxygen sparger and base pump. The culture is incubated for 3–4 days at which time the culture is coming out of log phase growth at $1-3\times10^6$ cells per ml. Thereafter, at 12 hour intervals, the medium is changed with PF-CHO medium (with custom modifications, JRH Biosciences). The first 2 collections are set aside as "washout". The third collection is the beginning of the production run. Sodium butyrate at final 2 mM is added every 48 hours to induce an increase in iduronidase expression. Production continues with medium changes of 10 liters every 12 hours and the collections filtered through a 1 micron filter to eliminate free cells and debris. The culture is monitored for temperature, pH and DO on a continuous basis. Twice daily, the culture is sampled before the medium change and assayed for cell condition and microorganisms by phase contrast microscopy, glucose content using a portable glucometer, iduronidase activity using a fluorescent substrate assay. Cell mass is assayed several times during the run using a total cellular protein assay. By the middle of the run, cell mass reaches $10^7$ cells per ml. Collected production medium containing iduronidase is then concentrated five fold using an A/G Technology hollow fiber molecular filter with a 30,000 molecular weight cutoff. The concentrate is then diafiltrated with a minimum three fold volume of 0.2 M NaCl in 10 mM $NaPO_4$, pH 5. 8 over a period of 8 hours. This step removes Pluronics F68 and uronic acids from the concentrate. These molecules can inhibit function of the Heparin column. The concentrate is adjusted to pH 5.0, filtered through 1.0 and 0.2 micron filters and then loaded on a Heparin-Sepharose CL-6B column. The column is washed with 10 column volumes of 0.2 M NaCl, 10 mM $NaPO_4$, pH 5.3), and the enzyme eluted with 0.6 MI, 10 m M$NaPO_4$,pH 5.8. The eluate is adjusted to 1.5 M NaCl, filtered through a 1 micron filter and loaded on a Phenyl-Sepharose HP column. The column is washed with 10 column volumes of 1.5 M NaCl, 10 mM $NaPO_4$, pH 5.8 and the enzyme eluted with 0.15 M NaCl, 10 mM $NaPO_4$, pH 5.8.

Viral inactivation is performed by acidifying the enzyme fraction to pH 3.3 using 1 M citric acid pH 2.9 and incubating the enzyme at pH 3.3 at room temperature for 4 hours and readjusting the pH to 5.8 using 1 M phosphate buffer. This step has been demonstrated to remove 5 logs or better of a retrovirus in spiking experiments. The inactivated enzyme is filtered through a $0.2\mu$ filter, concentrated on an A/G Technologies hollow fiber concentrator apparatus (30, 000 molecular weight cutoff) and injected in cycles on a Sephacryl S200 gel filtration column and the peaks collected. The pooled peaks are filtered through a $0.2\mu$ filter, formulated to 0.1 M $NaPO_4$, pH 5.8 and vialed.

A set of studies may be performed to assess the quality, purity, potency of the enzyme. Results of an SDS-PAGE analysis of the eluate is provided in FIG. 2.

One recombinant human α-L-iduronidase obtained from this procedure demonstrates a potency of 100,000 units per milliliter and has a total protein concentration of 0.313 mg/ml.

EXAMPLE 2

Seed train: A vial of working cell bank (WCB) CHO cells 2.131 is partially thawed in a 37° C. water bath. The thawed cells are added to seven mL of fresh cell culture medium (DMEM/F12) containing thymidine (7.6 mg/L), hypoxanthine (13.6 mg/L), G418 (375 mg/mL) and fetal bovine serum (5%). The cells are collected by gentle centrifugation (400 r.p.m. for 5 minutes). The pelleted cells are resuspended in fresh DMEM/F12 medium substituted as described above and the cells are placed in a T-75 cm flask in 25 mL of the medium.

After 2 to 3 days of incubation at 37° C. and 5% carbon dioxide, the cells are placed in a T-225 flask with 50 mL of fresh medium. The next split of cells is into a 250 mL spinner (100 mL of cells and medium) and the agitator (spinner) is rotated at 50 r.p.m. The inoculum volume and cell number is increased by a series of incubations (cell density increases) and subculturing (cell volume increases). The subculturing is performed such that the final cell density is between 2.0 and 2.5 $e^5$.

When the cells are cultured at 1 L volume (3 L spin flask), it is designed with both sparge and overlay gases and the gases are provided to the reactor using a standard aquarium pump, gas flow meters and the gases from the incubator internal atmosphere.

For bioreactors using the microporous microcarriers, the microcarriers are prepared as follows. The microcarriers are washed two times with phosphate buffered saline (PBS) and then autoclaved in PBS. The microcarriers are washed two times with JRH 325 (modified) medium (medium formulation as described above). The microcarriers are combined with sufficient fetal bovine serum such that the bioreactor will be 5% fetal bovine serum final. Medium (JRH 325 modified) is added to the microcarrier/fetal bovine serum solution and the mixture is pumped into the bioreactor. The substitution of microporous microcarriers in the production reactor provides the cells with a greater surface area for attached cell growth.

The cells are added to the microcarriers, and the reactor is run for three days with pH and dissolved oxygen control. Perfusion of the reactor with production medium (JRH 325 modified) is started when the glucose concentration in the reactor is reduced to 1.0 to 1.5 gm/L. The perfusion rate is gradually increased retaining glucose levels between 0.5 and 1.5 gm/L.

For bioreactors using single, cell suspension the seed train is prepared as described above. Using a single cell suspension simplifies bioreactor preparation and inoculation. The bioreactor is inoculated with cells in DMEM/F12 medium (25% of reactor volume) and JRH 325 modified (25% of reactor volume). Medium equal to 50% of the working reactor volume is added over 48 hours. Perfusion (and harvest) is started when cell density reaches $1.0\ e^6$ and the perfusion medium is the same as described above.

EXAMPLE 3

Recombinant iduronidase over-expressed in a Chinese Hamster Ovary (CHO) cell line, has been purified to near homogeneity following a 3 step column chromatography process. The first column involves an affinity chromatography step using Blue Sepharose 6 FF. The Blue eluate is then further purified by another affinity chromatography step using $Cu^{++}$ Chelating Sepharose FF. The final polish of the highly purified enzyme is achieved by hydrophobic interaction chromatography using Phenyl Sepharose High Performance (HP). The over-all yield ranges from 45 to 55 percent and the purity of the final product is >99%. The process is robust, reproducible, and scalable for large-scale manufacturing. The purified enzyme has been characterized with respect to its enzymatic activity using a fluorescence-based substrate, and its functional uptake by fibroblast cells. The enzyme has also been characterized for substrate specificity, carbohydrate profiles, and isoelectric focusing (IEF) profiles.

Outline of the Iduronidase Purification Process

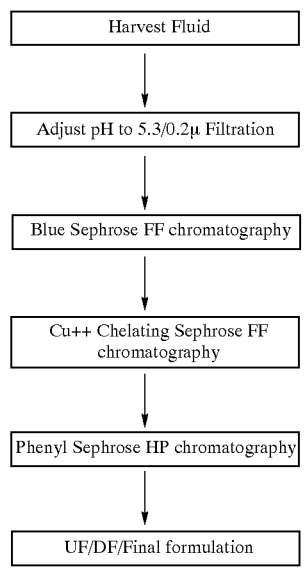

Sample Manipulation and Chromatography Purification pH Adjustment/Filtration

The pH of filtered harvest fluid (HF) is adjusted to 5.3 with 1 M $H_3PO_4$ and then filtered through a $0.45\mu$ filter (Sartoclean, Sartorius).

Blue Sepharose FF Chromatography

This affinity chromatography step serves to capture iduronidase to reduce the volume and to purify iduronidase by approximately seven to ten fold.

| | |
|---|---|
| Loading capacity: | 4 mg/ml (total protein per ml of resin) |
| Equilibration buffer: | 10 mM $NaPO_4$, pH 5.3 |
| Wash buffer: | 400 mM NaCl, 10 mM $NaPO_4$, pH 5.3 |
| Elution buffer: | 0.8 M NaCl, 10 mM $NaPO_4$, pH 5.3 |
| Regeneration buffer: | 2 M NaCl, 10 mM $NaPO_4$, pH 5.3 |
| Fold of purification: | 7–10 |
| Yield: | 70–85% |

$Cu^{++}$ Chelating Sepharose FF Chromatography

The $Cu^{++}$ Chelating affinity chromatography step is very effective for removing some contaminating CHO proteins. The inclusion of 10% glycerol in all the buffers seems to be crucial for the quantitative recovery of iduronidase.

| | |
|---|---|
| Loading capacity: | 2 mg/ml |
| Equilibration buffer: | 1 M NaCl, 25 mM NaAc, pH 6.0, 10% Glycerol |
| Wash buffer: | 1 M NaCl, 25 mM NaAc, pH 4.0, 10% Glycerol |
| Elution buffer: | 1 M NaCl, 25 mM NaAc, pH 3.7, 10% Glycerol |
| Regeneration buffer: | 1 M NaCl, 50 mM EDTA, pH 8.0 |
| Fold of purification: | 2–5 |
| Yield: | 80% |

Phenyl Sephrose HP Chromatography

Phenyl Sephrose is used as the last step to further purify the product as well as to reduce residual leached Cibacron blue dye and $Cu^{++}$ ion carried over from previous columns.

| | |
|---|---|
| Loading capacity: | 1 mg/ml |
| Equilibration buffer: | 2 M NaCl, 10 mM $NaPO_4$, pH 5.7 |
| Wash buffer: | 1.5 M NaCl, 10 mM $NaPO_4$, pH 5.7 |
| Elution buffer: | 0.7 M NaCl, 10 mM $NaPO_4$, pH 5.7 |
| Regeneration buffer: | 0 M NaCl, 10 mM $NaPO_4$, pH 5.7 |
| Fold of purification: | 1.5 |
| Yield: | 90% |

Ultrafiltration (UF)/Diafiltration (DF)/Final Formulation

The purified iduronidase is concentrated and diafiltered to a final concentration of 1 mg/ml in formulation buffer (150 mM NaCl, 100 mM $NaPO_4$, pH 5.8) using a TFF system (Sartocon Slice) from Sartorius. The enzyme is then sterilized by filtering through 0.2 micron CA filter and injected into sterile vials.

Characterization of Purified Iduronidase

Analysis of enzyme purity using SDS-PAGE stained with Coomassie Blue or Silver and Western blot analysis. Analysis of enzymatic activity using 4MU-sulfate as substrate. Analysis of functional uptake using fibroblast cell assay. Analysis of carbohydrates by FACE. Analysis of IEF profiles.

| Test | Procedure | Specification |
|---|---|---|
| Appearance | Visual | Clear, colorless |
| Identity | SDS PAGE/Western blot | Reaction to Anti-Idu |
| Purity | SDS PAGE | >99% |
| Protein Concentration | BCA/UV | |
| Activity | Fluorescent assay | |

| Test | Procedure | Specification |
| --- | --- | --- |
| Specific Activity | Fluorescence/BCA or UV | 125–130,000 units/mg |
| Carbohydrate | FACE | |
| pI | IEF | |

EXAMPLE 4

Short-term intravenous administration of purified human recombinant α-L-iduronidase to 9 MPS I dogs and 6 MPS I cats has shown significant uptake of enzyme in a variety of tissues with an estimated 50% or more recovery in tissues 24 hours after a single dose. Although liver and spleen take up the largest amount of enzyme, and have the best pathologic improvement, improvements in pathology and glycosaminoglycan content has been observed in many, but not all tissues. In particular, the cartilage, brain and heart valve did not have significant improvement. Clinical improvement was observed in a single dog on long-term treatment for 13 months, but other studies have been limited to 6 months or less. All dogs, and most cats, that received recombinant human enzyme developed antibodies to the human product. The IgG antibodies are of the complement activating type (probable canine IgG equivalent). This phenomena is also observed in at least 13% of alglucerase-treated Gaucher patients. Proteinuria has been observed in one dog which may be related to immune complex disease. No other effects of the antibodies have been observed in the other treated animals. Specific toxicity was not observed and clinical laboratory studies (complete blood counts, electrolytes, BUN/creatinine, liver enzymes, urinalysis) have been otherwise normal.

Enzyme therapy at even small doses of 25,000 units (0.1 mg/kg/wk) resulted in significant enzyme distribution to some tissues and decreases in GAG storage. If continued for over 1 year, significant clinical effects of the therapy were evident in terms of activity, mobility, growth and overall health. The therapy at this dose did not improve other tissues that are important sites for disease in this entity such as cartilage and brain. Higher doses of 125,000 units (0.5 mg/kg) given 5 times over two weeks demonstrate that improved tissue penetration can be achieved and a therapeutic effect at the tissue level was accomplished in as little as 2 weeks. Studies at this increased dose are ongoing in two dogs for six months to date. These MPS I dogs are showing significant clinical improvement and substantial decreases in urinary GAG excretion into the normal range. Other than an immune reaction controlled by altered administration techniques, the enzyme therapy has not shown significant clinical or biochemical toxicity. Enzyme therapy at this higher weekly dose is effective at improving, some clinical features of MPS I and decreasing storage without significant toxicity.

The results of these various studies in MPS I dogs and one study in MPS I cats shows that human recombinant α-L-iduronidase is safe. These same results also provide a significant rationale that this recombinant enzyme should be effective in treating α-L-iduronidase deficiency.

EXAMPLE 5

The human cDNA of α-L-iduronidase predicts a protein of 653 amino acids and an expected molecular weight of 70,000 daltons after signal peptide cleavage. Amino acid sequencing reveals alanine 26 at the N-terminus giving an expected protein of 629 amino acids. Human recombinant α-L-iduronidase has a Histidine at position 8 of the mature protein. The predicted protein sequence comprises six potential N-linked oligosaccharide modification sites. All of these sites are modified in the recombinant protein. The third and sixth sites have been demonstrated to contain one or more mannose 6-phosphate residues responsible for high affinity uptake into cells.

This peptide corresponds to Amino Acids 26–45 of Human Recombinant α-L-iduronidase with an N-terminus alanine and the following sequence:

ala-glu-ala-pro-his-leu-val-his-val-asp-ala-ala-arg-ala-leu-trp-pro-leu-arg-arg

The recombinant enzyme has an apparent molecular weight of 82,000 daltons on SDS-PAGE due to carbohydrate modifications. Purified human recombinant α-L-iduronidase has been sequenced by the UCLA Protein Sequencing facility. It is preferred to administer the recombinant enzyme intravenously. Human recombinant α-L-iduronidase was supplied in 10 mL polypropylene vials at a concentration of 0.05–0.2 mg/ml (12,500–50,000 units per mL.). The final dosage form of the enzyme includes human recombinant α-L-iduronidase, normal saline, phosphate buffer at pH 5.8 and human albumin at 1 mg/ml. These are prepared in a bag of normal saline.

| Component | Composition |
| --- | --- |
| α-L-iduronidase | 0.05–0.2 mg/mL or 12,500–50,000 units per mL |
| Sodium chloride solution | 150 mM in an IV bag, 50–250 cc total volume |
| Sodium phosphate buffer | 10–50 mM, pH 5.8 |
| Human albumin | 1 mg/mL |

Figure 3:
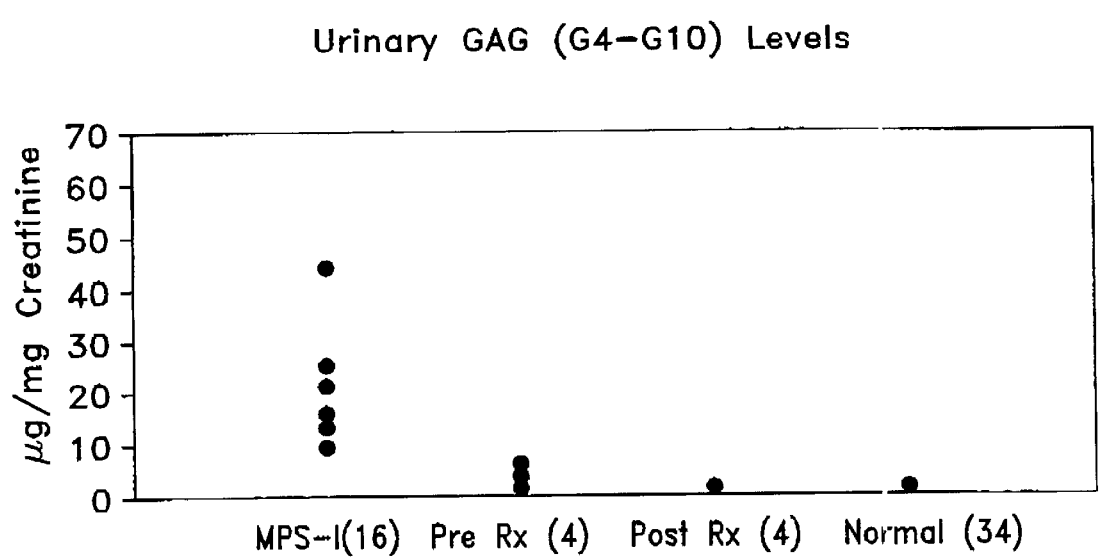
FIG. 3 reveals the urinary GAG levels in 16 MPS I patients in relation to normal excretion values. There is a wide range of urine GAG values in untreated MPS I patients. A greater than 50% reduction in excretion of undegraded GAGs following therapy with recombinant α-L-iduronidase is a valid means to measure an individual's response to therapy.
Figure 4:
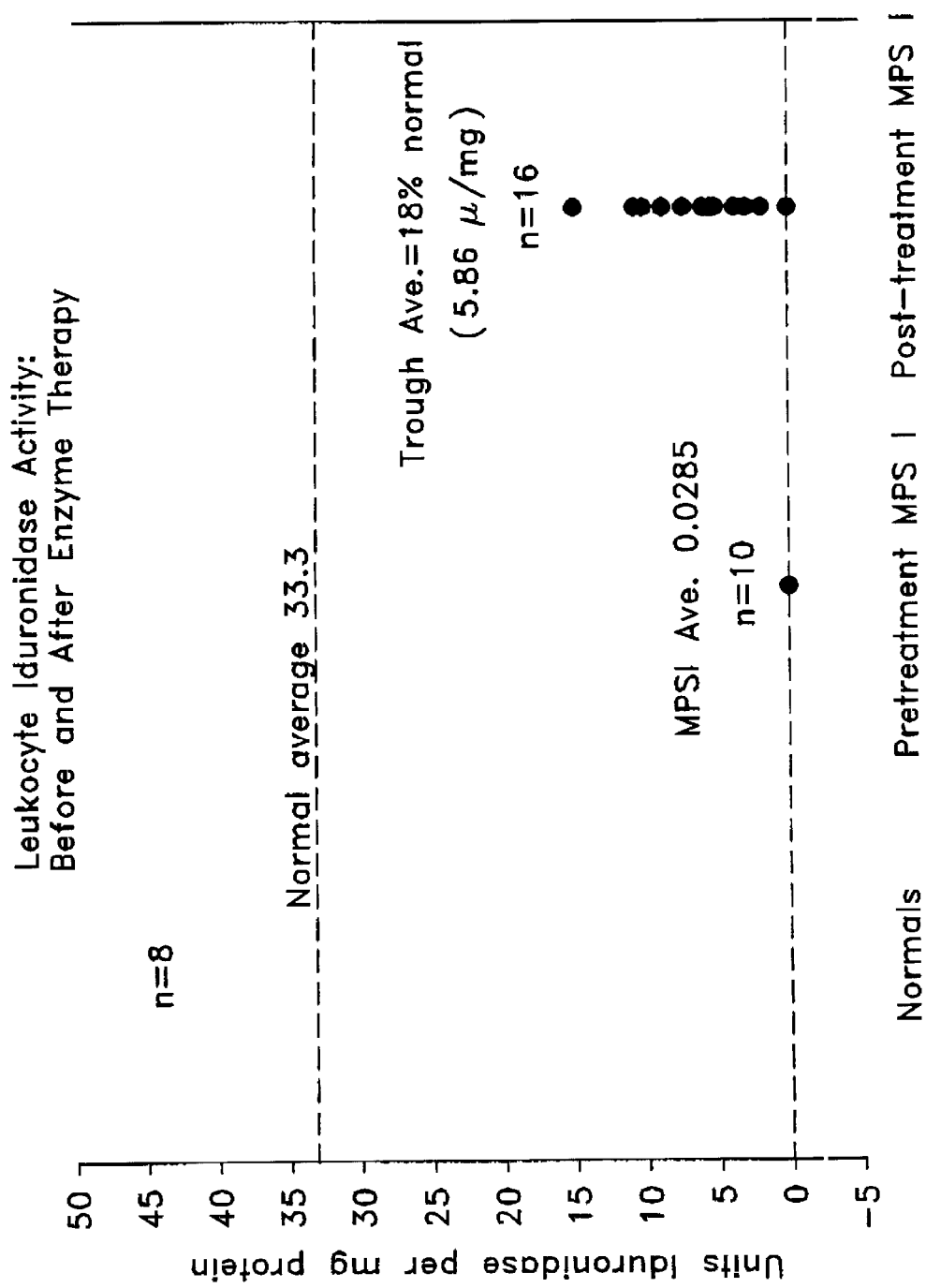
FIG. 4 demonstrates leukocyte iduronidase activity before and after enzyme therapy in MPS I patients.
Figure 5:
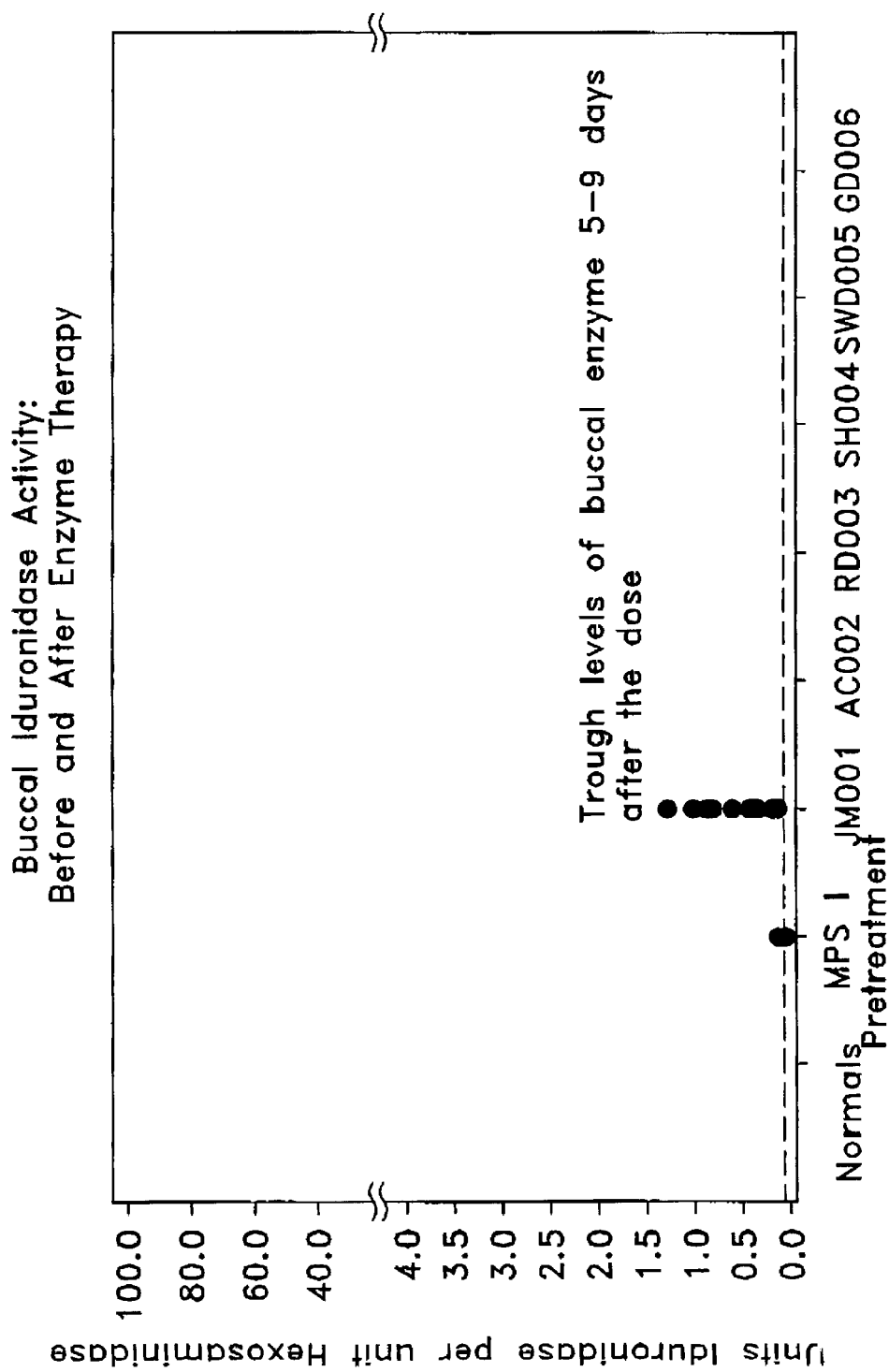
FIG. 5 demonstrates the buccal iduronidase activity before and after enzyme therapy.
Figure 6:
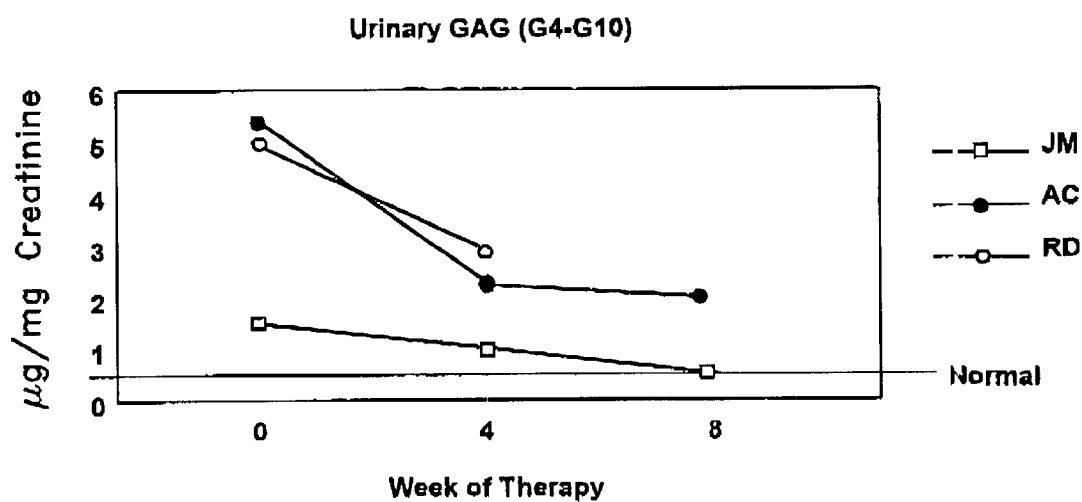
FIG. 6 demonstrates in three patients that a substantial shrinkage of liver and spleen together with significant clinical improvement in joint and soft tissue storage was associated with a greater than 65% reduction in undegraded GAG after only 8 weeks of treatment with recombinant enzyme.
Figure 7A:
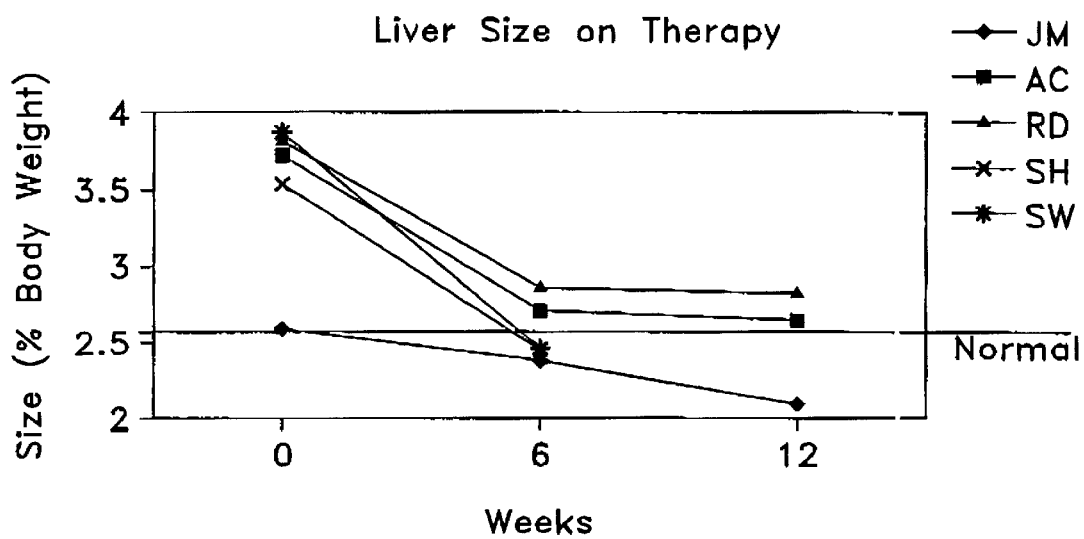
FIG. 7 demonstrates that there is substantial normalization of livers and spleens in patients treated with recombinant enzyme after only 12 weeks of therapy.
Figure 7B:
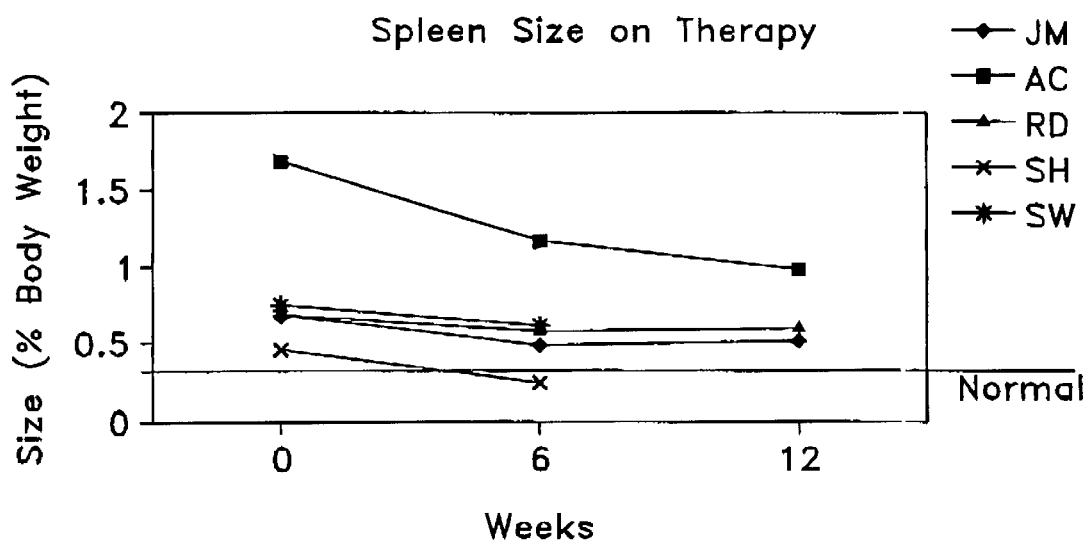
Figure 8:
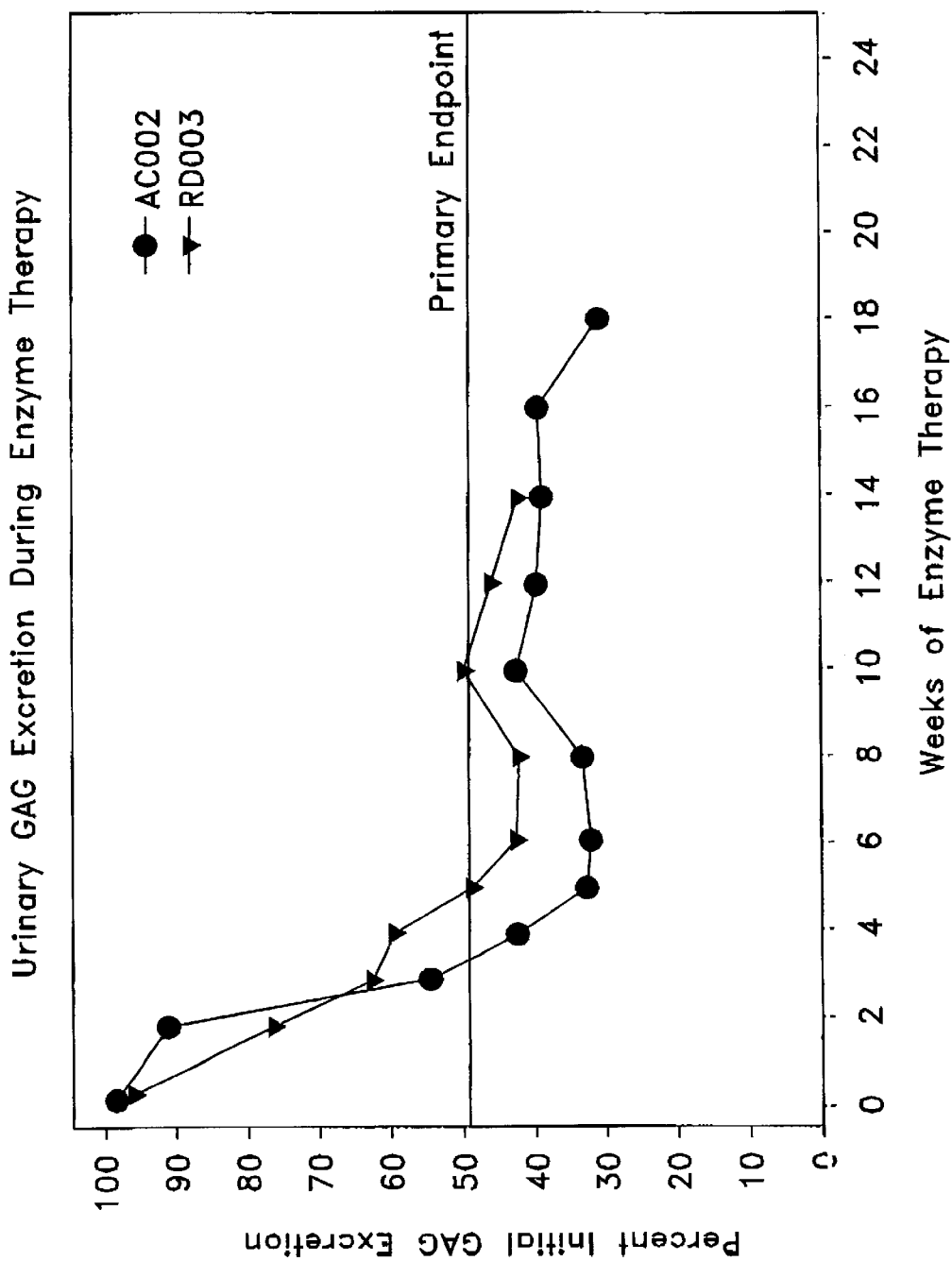
FIG. 8 demonstrates a precipitous drop in urinary GAG excretion over 22 weeks of therapy with recombinant enzyme in 6 patients.
Figure 4:
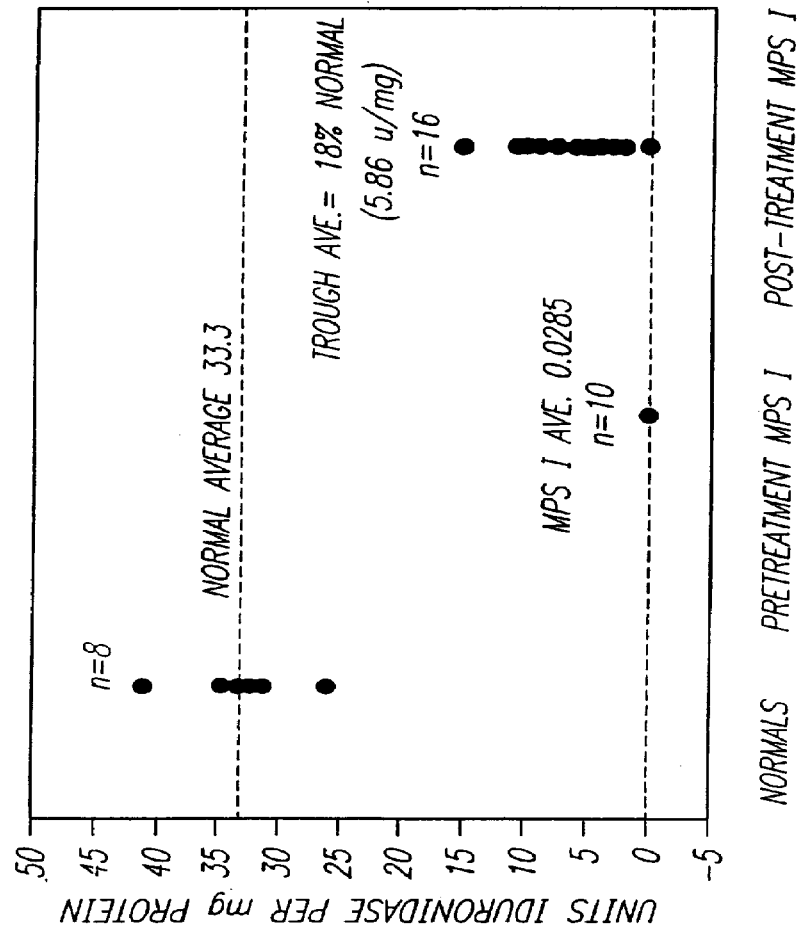
Figure 5:
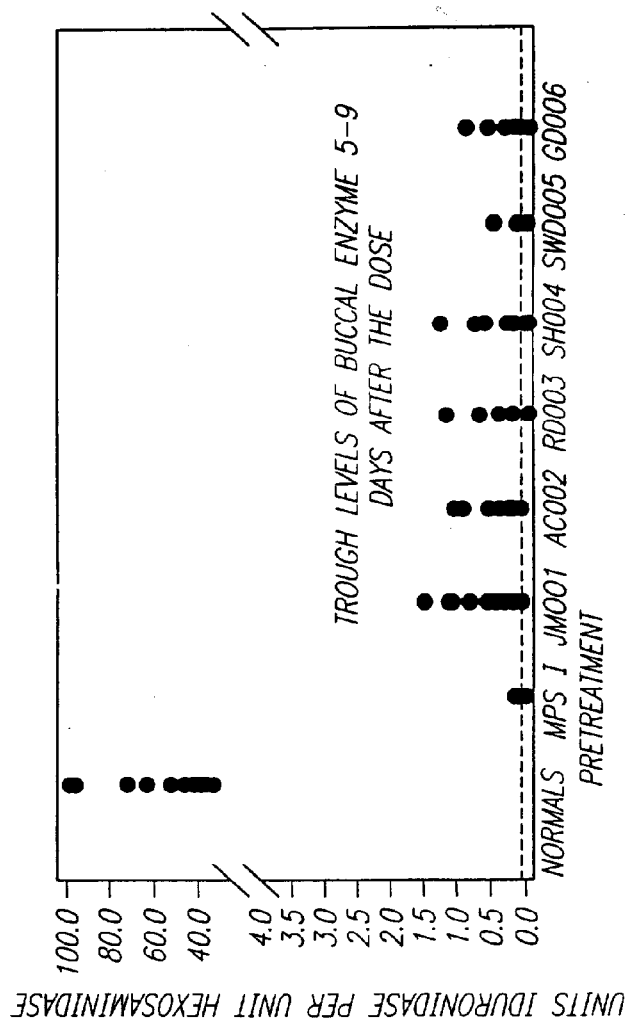
Figure 8:
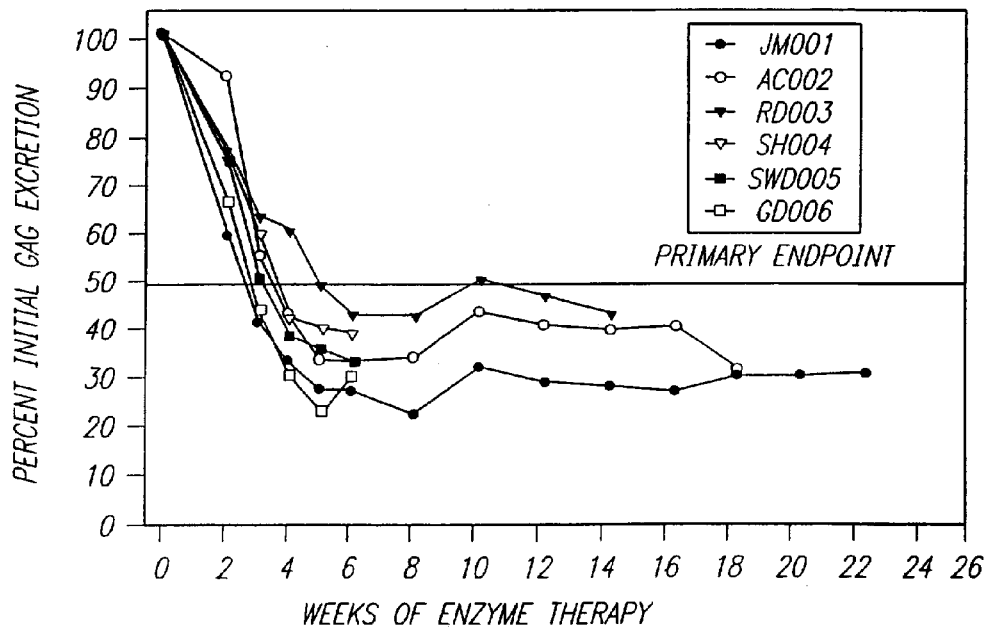

Human patients manifesting a clinical phenotype of MPS-I disorder with an α-L-iduronidase level of less than 1% of normal in leukocytes and fibroblasts were included in the study. All patients manifested some clinical evidence of visceral and soft tissue accumulation of glycosaminoglycans with varying degrees of functional impairment. Efficacy was determined by measuring the percentage reduction in urinary GAG excretion over time. FIG. 3 reveals the urinary GAG levels in 16 MPS-I patients in relation to normal excretion values. There is a wide range of urine GAG values in untreated MPS-I patients. A greater than 50% reduction in excretion of undegraded GAGs following therapy with recombinant α-L-iduronidase is a valid means to measure an individual's response to therapy. FIG. 4 demonstrates leukocyte iduronidase activity before and after enzyme therapy in MPS I patients. The buccal iduronidase activity before and after enzyme therapy is depicted in FIG. 5. FIG. 6 demonstrates in three patients that a substantial shrinkage of liver and spleen together with significant clinical improvement in joint and soft tissue storage was associated with a greater than 65% reduction in undegraded GAG after only 8 weeks of treatment with recombinant enzyme. FIG. 7 demonstrates that there is substantial normalization of livers and spleens in patients treated with recombinant enzyme after only 12 weeks of therapy with recombinant enzyme. FIG. 8 demonstrates a precipitous drop in urinary GAG excretion over 22 weeks of therapy with recombinant enzyme in 11 patients. Clinical assessment of liver and spleen size has been the most widely accepted means for evaluating successful bone marrow transplant treatment in MPS-I patients (Hoogerbrugge et al., *Lancet* 345:1398 (1995)). Such measurements are highly correlated with a decreased visceral storage of GAGs in MPS-I patients.

Although the invention has been described with reference to the presently preferred embodiments, it should be understood that various modifications can be made without departing from the spirit of the invention. Accordingly, the invention is limited only by the following claims.

SEQUENCE LISTING

<160> NUMBER OF SEQ ID NOS: 2

<210> SEQ ID NO 1
<211> LENGTH: 6200
<212> TYPE: DNA
<213> ORGANISM: Homo sapiens
<220> FEATURE:
<221> NAME/KEY: CDS
<222> LOCATION: (1558)...(3516)

<400> SEQUENCE: 1

| | | |
|---|---|---|
| gacggatcgg gagatctccc gatcccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacgggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aatgtcgta acaactccgc cccattgacg caaatgggcg | 780 |
| gtaggcgtgt acggtgggag gtctatataa gcagagctct ctggctaact agagaaccca | 840 |
| ctgcttaact ggcttatcga aattaatacg actcactata gggagaccca gcttcgcag | 900 |
| aattcctgcg gctgctacag tgtgtccagc gtcctgcctg gctgtgctga gcgctggaac | 960 |
| agtggcgcat cattcaagtg cacagttacc catcctgagt ctggcacctt aactggcaca | 1020 |
| attgccaaag tcacaggtga gctcagatgc ataccaggac attgtatgac gttccctgct | 1080 |
| cacatgcctg ctttcttcct ataatacaga tggtcaacta actgctcatg tccttatatc | 1140 |
| acagagggaa attggagcta tctgaggaac tgcccagaag ggaagggcag aggggtcttg | 1200 |
| ctctccttgt ctgagccata actcttcttt ctaccttcca gtgaacacct tcccaccca | 1260 |
| ggtccacctg ctaccgccgc cgtcggagga gctggccctg aatgagctct tgtccctgac | 1320 |
| atgcctggtg cgagctttca accctaaaga agtgctggtg cgatggctgc atggaaatga | 1380 |
| ggagctgtcc ccagaaagct acctagtgtt tgagccccta aggagccag gcgagggagc | 1440 |
| caccacctac ctggtgacaa gcgtgttgcg tgtatcagct gaaagcttga tatcgaattc | 1500 |
| cggaggcgga accggcagtg cagcccgaag ccccgcagtc cccgagcacg cgtggcc atg | 1560 |
|  | Met |
|  | 1 |
| cgt ccc ctg cgc ccc cgc gcc gcg ctg ctg gcg ctc ctg gcc tcg ctc | 1608 |
| Arg Pro Leu Arg Pro Arg Ala Ala Leu Leu Ala Leu Leu Ala Ser Leu |  |
| 5 10 15 |  |
| ctg gcc gcg ccc ccg gtg gcc ccg gcc gag gcc ccg cac ctg gtg cat | 1656 |
| Leu Ala Ala Pro Pro Val Ala Pro Ala Glu Ala Pro His Leu Val His |  |
| 20 25 30 |  |
| gtg gac gcg gcc cgc gcg ctg tgg ccc ctg cgg cgc ttc tgg agg agc | 1704 |
| Val Asp Ala Ala Arg Ala Leu Trp Pro Leu Arg Arg Phe Trp Arg Ser |  |

-continued

| | | | | | | | | | | | | | | | |
|---|---|---|---|---|---|---|---|---|---|---|---|---|---|---|---|
| | | 35 | | | | | 40 | | | | | 45 | | | |
| aca | ggc | ttc | tgc | ccc | ccg | ctg | cca | cac | agc | cag | gct | gac | cag | tac | gtc | 1752 |
| Thr | Gly | Phe | Cys | Pro | Pro | Leu | Pro | His | Ser | Gln | Ala | Asp | Gln | Tyr | Val |
| 50 | | | | | 55 | | | | | 60 | | | | | 65 |
| ctc | agc | tgg | gac | cag | cag | ctc | aac | ctc | gcc | tat | gtg | ggc | gcc | gtc | cct | 1800 |
| Leu | Ser | Trp | Asp | Gln | Gln | Leu | Asn | Leu | Ala | Tyr | Val | Gly | Ala | Val | Pro |
| | | | | 70 | | | | | 75 | | | | | 80 | |
| cac | cgc | ggc | atc | aag | cag | gtc | cgg | acc | cac | tgg | ctg | ctg | gag | ctt | gtc | 1848 |
| His | Arg | Gly | Ile | Lys | Gln | Val | Arg | Thr | His | Trp | Leu | Leu | Glu | Leu | Val |
| | | | | 85 | | | | | 90 | | | | | 95 | |
| acc | acc | agg | ggg | tcc | act | gga | cgg | ggc | ctg | agc | tac | aac | ttc | acc | cac | 1896 |
| Thr | Thr | Arg | Gly | Ser | Thr | Gly | Arg | Gly | Leu | Ser | Tyr | Asn | Phe | Thr | His |
| | | | 100 | | | | | 105 | | | | | 110 | | |
| ctg | gac | ggg | tac | ctg | gac | ctt | ctc | agg | gag | aac | cag | ctc | ctc | cca | ggg | 1944 |
| Leu | Asp | Gly | Tyr | Leu | Asp | Leu | Leu | Arg | Glu | Asn | Gln | Leu | Leu | Pro | Gly |
| | 115 | | | | | 120 | | | | | 125 | | | | |
| ttt | gag | ctg | atg | ggc | agc | gcc | tcg | ggc | cac | ttc | act | gac | ttt | gag | gac | 1992 |
| Phe | Glu | Leu | Met | Gly | Ser | Ala | Ser | Gly | His | Phe | Thr | Asp | Phe | Glu | Asp |
| 130 | | | | | 135 | | | | | 140 | | | | | 145 |
| aag | cag | cag | gtg | ttt | gag | tgg | aag | gac | ttg | gtc | tcc | agc | ctg | gcc | agg | 2040 |
| Lys | Gln | Gln | Val | Phe | Glu | Trp | Lys | Asp | Leu | Val | Ser | Ser | Leu | Ala | Arg |
| | | | | 150 | | | | | 155 | | | | | 160 | |
| aga | tac | atc | ggt | agg | tac | gga | ctg | gcg | cat | gtt | tcc | aag | tgg | aac | ttc | 2088 |
| Arg | Tyr | Ile | Gly | Arg | Tyr | Gly | Leu | Ala | His | Val | Ser | Lys | Trp | Asn | Phe |
| | | | | 165 | | | | | 170 | | | | | 175 | |
| gag | acg | tgg | aat | gag | cca | gac | cac | cac | gac | ttt | gac | aac | gtc | tcc | atg | 2136 |
| Glu | Thr | Trp | Asn | Glu | Pro | Asp | His | His | Asp | Phe | Asp | Asn | Val | Ser | Met |
| | | | 180 | | | | | 185 | | | | | 190 | | |
| acc | atg | caa | ggc | ttc | ctg | aac | tac | tac | gat | gcc | tgc | tcg | gag | ggt | ctg | 2184 |
| Thr | Met | Gln | Gly | Phe | Leu | Asn | Tyr | Tyr | Asp | Ala | Cys | Ser | Glu | Gly | Leu |
| | 195 | | | | | 200 | | | | | 205 | | | | |
| cgc | gcc | gcc | agc | ccc | gcc | ctg | cgg | ctg | gga | ggc | ccc | ggc | gac | tcc | ttc | 2232 |
| Arg | Ala | Ala | Ser | Pro | Ala | Leu | Arg | Leu | Gly | Gly | Pro | Gly | Asp | Ser | Phe |
| 210 | | | | | 215 | | | | | 220 | | | | | 225 |
| cac | agg | cca | ccg | cga | tcc | ccg | ctg | agc | tgg | ggc | ctc | ctg | cgc | cac | tgc | 2280 |
| His | Arg | Pro | Pro | Arg | Ser | Pro | Leu | Ser | Trp | Gly | Leu | Leu | Arg | His | Cys |
| | | | | 230 | | | | | 235 | | | | | 240 | |
| cac | gac | ggt | acc | aac | ttc | ttc | act | ggg | gag | gcg | ggc | gtg | cgg | ctg | gac | 2328 |
| His | Asp | Gly | Thr | Asn | Phe | Phe | Thr | Gly | Glu | Ala | Gly | Val | Arg | Leu | Asp |
| | | | 245 | | | | | 250 | | | | | 255 | | |
| tac | atc | tcc | ctc | cac | agg | aag | ggt | gcg | cgc | agc | tcc | atc | tcc | atc | ctg | 2376 |
| Tyr | Ile | Ser | Leu | His | Arg | Lys | Gly | Ala | Arg | Ser | Ser | Ile | Ser | Ile | Leu |
| | 260 | | | | | 265 | | | | | 270 | | | | |
| gag | cag | gag | aag | gtc | gtc | gcg | cag | cag | atc | cgg | cag | ctc | ttc | ccc | aag | 2424 |
| Glu | Gln | Glu | Lys | Val | Val | Ala | Gln | Gln | Ile | Arg | Gln | Leu | Phe | Pro | Lys |
| 275 | | | | | 280 | | | | | 285 | | | | | |
| ttc | gcg | gac | acc | ccc | att | tac | aac | gac | gag | gcg | gac | ccg | ctg | gtg | ggc | 2472 |
| Phe | Ala | Asp | Thr | Pro | Ile | Tyr | Asn | Asp | Glu | Ala | Asp | Pro | Leu | Val | Gly |
| 290 | | | | 295 | | | | | 300 | | | | | 305 | |
| tgg | tcc | ctg | cca | cag | ccg | tgg | agg | gcg | gac | gtg | acc | tac | gcg | gcc | atg | 2520 |
| Trp | Ser | Leu | Pro | Gln | Pro | Trp | Arg | Ala | Asp | Val | Thr | Tyr | Ala | Ala | Met |
| | | | 310 | | | | | 315 | | | | | 320 | | |
| gtg | gtg | aag | gtc | atc | gcg | cag | cat | cag | aac | ctg | cta | ctg | gcc | aac | acc | 2568 |
| Val | Val | Lys | Val | Ile | Ala | Gln | His | Gln | Asn | Leu | Leu | Leu | Ala | Asn | Thr |
| | | 325 | | | | | 330 | | | | | 335 | | | |
| acc | tcc | gcc | ttc | ccc | tac | gcg | ctc | ctg | agc | aac | gac | aat | gcc | ttc | ctg | 2616 |
| Thr | Ser | Ala | Phe | Pro | Tyr | Ala | Leu | Leu | Ser | Asn | Asp | Asn | Ala | Phe | Leu |
| | 340 | | | | | 345 | | | | | 350 | | | | |
| agc | tac | cac | ccg | cac | ccc | ttc | gcg | cag | cgc | acg | ctc | acc | gcg | cgc | ttc | 2664 |

```
                                                                                           -continued Ser Tyr His Pro His Pro Phe Ala Gln Arg Thr Leu Thr Ala Arg Phe
    355                 360                 365 cag gtc aac aac acc cgc ccg ccg cac gtg cag ctg ttg cgc aag ccg         2712
Gln Val Asn Asn Thr Arg Pro Pro His Val Gln Leu Leu Arg Lys Pro
370                 375                 380                 385 gtg ctc acg gcc atg ggg ctg ctg gcg ctg ctg gat gag gag cag ctc         2760
Val Leu Thr Ala Met Gly Leu Leu Ala Leu Leu Asp Glu Glu Gln Leu
                    390                 395                 400 tgg gcc gaa gtg tcg cag gcc ggg acc gtc ctg gac agc aac cac acg         2808
Trp Ala Glu Val Ser Gln Ala Gly Thr Val Leu Asp Ser Asn His Thr
                405                 410                 415 gtg ggc gtc ctg gcc agc gcc cac cgc ccc cag ggc ccg gcc gac gcc         2856
Val Gly Val Leu Ala Ser Ala His Arg Pro Gln Gly Pro Ala Asp Ala
            420                 425                 430 tgg cgc gcc gcg gtg ctg atc tac gcg agc gac gac acc cgc gcc cac         2904
Trp Arg Ala Ala Val Leu Ile Tyr Ala Ser Asp Asp Thr Arg Ala His
        435                 440                 445 ccc aac cgc agc gtc gcg gtg acc ctg cgg ctg cgc ggg gtg ccc ccc         2952
Pro Asn Arg Ser Val Ala Val Thr Leu Arg Leu Arg Gly Val Pro Pro
450                 455                 460                 465 ggc ccg ggc ctg gtc tac gtc acg cgc tac ctg gac aac ggg ctc tgc         3000
Gly Pro Gly Leu Val Tyr Val Thr Arg Tyr Leu Asp Asn Gly Leu Cys
                    470                 475                 480 agc ccc gac ggc gag tgg cgg cgc ctg ggc cgg ccc gtc ttc ccc acg         3048
Ser Pro Asp Gly Glu Trp Arg Arg Leu Gly Arg Pro Val Phe Pro Thr
                485                 490                 495 gca gag cag ttc cgg cgc atg cgc gcg gct gag gac ccg gtg gcc gcg         3096
Ala Glu Gln Phe Arg Arg Met Arg Ala Ala Glu Asp Pro Val Ala Ala
            500                 505                 510 gcg ccc cgc ccc tta ccc gcc ggc ggc cgc ctg acg ctg cgc ccc gcg         3144
Ala Pro Arg Pro Leu Pro Ala Gly Gly Arg Leu Thr Leu Arg Pro Ala
        515                 520                 525 ctg cgg ctg ccg tcg ctt ttg ctg gtg cac gtg tgt gcg cgc ccc gag         3192
Leu Arg Leu Pro Ser Leu Leu Leu Val His Val Cys Ala Arg Pro Glu
530                 535                 540                 545 aag ccg ccc ggg cag gtc acg cgg ctc cgc gcc ctg ccc ctg acc caa         3240
Lys Pro Pro Gly Gln Val Thr Arg Leu Arg Ala Leu Pro Leu Thr Gln
                    550                 555                 560 ggg cag ctg gtt ctg gtc tgg tcg gat gaa cac gtg ggc tcc aag tgc         3288
Gly Gln Leu Val Leu Val Trp Ser Asp Glu His Val Gly Ser Lys Cys
                565                 570                 575 ctg tgg aca tac gag atc cag ttc tct cag gac ggt aag gcg tac acc         3336
Leu Trp Thr Tyr Glu Ile Gln Phe Ser Gln Asp Gly Lys Ala Tyr Thr
            580                 585                 590 ccg gtc agc agg aag cca tcg acc ttc aac ctc ttt gtg ttc agc cca         3384
Pro Val Ser Arg Lys Pro Ser Thr Phe Asn Leu Phe Val Phe Ser Pro
        595                 600                 605 gac aca ggt gct gtc tct ggc tcc tac cga gtt cga gcc ctg gac tac         3432
Asp Thr Gly Ala Val Ser Gly Ser Tyr Arg Val Arg Ala Leu Asp Tyr
610                 615                 620                 625 tgg gcc cga cca ggc ccc ttc tcg gac cct gtg ccg tac ctg gag gtc         3480
Trp Ala Arg Pro Gly Pro Phe Ser Asp Pro Val Pro Tyr Leu Glu Val
                    630                 635                 640 cct gtg cca aga ggg ccc cca tcc ccg ggc aat cca tgagcctgtg              3526
Pro Val Pro Arg Gly Pro Pro Ser Pro Gly Asn Pro
                645                 650 ctgagcccca gtgggttgca cctccaccgg cagtcagcga gctggggctg cactgtgccc       3586
atgctgccct cccatcaccc cctttgcaat atattttat attttaaaaa aaaaaaaaa         3646
```

```
aaaaaaaaaa aaaaaaaaaa aaaaaaaaaa aaaaaaaaaa aaaaaaaaaa aaagaattcc    3706
tgcagcccgg gggatccact agttctagag ggcccgttta aacccgctga tcagcctcga    3766
ctgtgccttc tagttgccag ccatctgttg tttgccccct ccccgtgcct tccttgaccc    3826
tggaaggtgc cactcccact gtcctttcct aataaaatga ggaaattgca tcgcattgtc    3886
tgagtaggtg tcattctatt ctgggggtg gggtggggca ggacagcaag ggggaggatt     3946
gggaagacaa tagcaggcat gctggggatg cggtgggctc tatggcttct gaggcggaaa    4006
gaaccagctg gggctcgaga gcttggcgta atcatggtca tagctgtttc ctgtgtgaaa    4066
ttgttatccg ctcacaattc cacacaacat acgagccgga agcataaagt gtaaagcctg    4126
gggtgcctaa tgagtgagct aactcacatt aattgcgttg cgctcactgc ccgctttcca    4186
gtcgggaaac ctgtcgtgcc agctgcatta atgaatcggc caacgcgcgg ggagaggcgg    4246
tttgcgtatt gggcgctctt ccgcttcctc gctcactgac tcgctgcgct cggtcgttcg    4306
gctgcggcga gcggtatcag ctcactcaaa ggcggtaata cggttatcca cagaatcagg    4366
ggataacgca ggaaagaaca tgtgagcaaa aggccagcaa aaggccagga accgtaaaaa    4426
ggccgcgttg ctggcgtttt tccataggct ccgcccccct gacgagcatc acaaaaatcg    4486
acgctcaagt cagaggtggc gaaacccgac aggactataa agataccagg cgtttccccc    4546
tggaagctcc ctggtgcgct ctcctgttcc gaccctgccg cttaccggat acctgtccgc    4606 cttctccct cgggaagcg tggcgctttt tcaatgctca cgctgtaggt atctcagttc      4666
ggtgtaggtc gttcgctcca agctgggctg tgtgcacgaa ccccccgttc agcccgaccg    4726
ctgcgcctta tccggtaact atcgtcttga gtccaacccg gtaagacacg acttatcgcc    4786
actggcagca gccactggta acaggattag cagagcgagg tatgtaggcg gtgctacaga    4846
gttcttgaag tggtggccta actacggcta cactagaagg acagtatttg gtatctgcgc    4906
tctgctgaag ccagttacct tcggaaaaag agttggtagc tcttgatccg gcaaacaaac    4966
caccgctggt agcggtggtt tttttgtttg caagcagcag attacgcgca gaaaaaaagg    5026
atctcaagaa gatcctttga tcttttctac ggggtctgac gctcagtgga acgaaaactc    5086
acgttaaggg attttggtca tgagattatc aaaaggatc ttcacctaga tccttttaaa     5146
ttaaaaatga agttttaaat caatctaaag tatatatgag taaacttggt ctgacagtta    5206
ccaatgctta atcagtgagg cacctatctc agcgatctgt ctatttcgtt catccatagt    5266
tgcctgactc cccgtcgtgt agataactac gatacgggag ggcttaccat ctggccccag    5326
tgctgcaatg ataccgcgag acccacgctc accggctcca gatttatcag caataaacca    5386
gccagccgga agggccgagc gcagaagtgg tcctgcaact ttatccgcct ccatccagtc    5446
tattaattgt tgccgggaag ctagagtaag tagttcgcca gttaatagtt tgcgcaacgt    5506
tgttgccatt gctacaggca tcgtggtgtc acgctcgtcg tttggtatgg cttcattcag    5566
ctccggttcc caacgatcaa ggcgagttac atgatccccc atgttgtgca aaaagcggt    5626 tagctccttc ggtcctccga tcgttgtcag aagtaagttg gccgcagtgt tatcactcat    5686
ggttatggca gcactgcata attctgttac tgtcatgcca tccgtaagat gcttttctgt    5746
gactggtgag tactcaacca agtcattctg agaatagtgt atgcggcgac cgagttgctc    5806
ttgcccggcg tcaatacggg ataataccgc gccacatagc agaactttaa aagtgctcat    5866
cattggaaaa cgttcttcgg ggcgaaaact ctcaaggatc ttaccgctgt tgagatccag    5926
ttcgatgtaa cccactcgtg cacccaactg atcttcagca tcttttactt tcaccagcgt    5986
ttctgggtga gcaaaaacag gaaggcaaaa tgccgcaaaa aagggaataa gggcgacacg    6046
```

```
gaaatgttga atactcatac tcttcctttt tcaatattat tgaagcattt atcagggtta    6106
ttgtctcatg agcggataca tatttgaatg tatttagaaa aataaacaaa tagggggttcc    6166 gcgcacattt ccccgaaaag tgccacctga cgtc                                6200
```

<210> SEQ ID NO 2
<211> LENGTH: 653
<212> TYPE: PRT
<213> ORGANISM: Homo sapiens

<400> SEQUENCE: 2

```
Met Arg Pro Leu Arg Pro Arg Ala Ala Leu Leu Ala Leu Leu Ala Ser
 1               5                  10                  15

Leu Leu Ala Ala Pro Pro Val Ala Pro Ala Glu Ala Pro His Leu Val
                20                  25                  30

His Val Asp Ala Ala Arg Ala Leu Trp Pro Leu Arg Arg Phe Trp Arg
            35                  40                  45

Ser Thr Gly Phe Cys Pro Pro Leu Pro His Ser Gln Ala Asp Gln Tyr
        50                  55                  60

Val Leu Ser Trp Asp Gln Gln Leu Asn Leu Ala Tyr Val Gly Ala Val
 65                  70                  75                  80

Pro His Arg Gly Ile Lys Gln Val Arg Thr His Trp Leu Leu Glu Leu
                85                  90                  95

Val Thr Thr Arg Gly Ser Thr Gly Arg Gly Leu Ser Tyr Asn Phe Thr
                100                 105                 110

His Leu Asp Gly Tyr Leu Asp Leu Leu Arg Glu Asn Gln Leu Leu Pro
            115                 120                 125

Gly Phe Glu Leu Met Gly Ser Ala Ser Gly His Phe Thr Asp Phe Glu
        130                 135                 140

Asp Lys Gln Gln Val Phe Glu Trp Lys Asp Leu Val Ser Ser Leu Ala
145                 150                 155                 160

Arg Arg Tyr Ile Gly Arg Tyr Gly Leu Ala His Val Ser Lys Trp Asn
                165                 170                 175

Phe Glu Thr Trp Asn Glu Pro Asp His His Asp Phe Asp Asn Val Ser
                180                 185                 190

Met Thr Met Gln Gly Phe Leu Asn Tyr Tyr Asp Ala Cys Ser Glu Gly
            195                 200                 205

Leu Arg Ala Ala Ser Pro Ala Leu Arg Leu Gly Gly Pro Gly Asp Ser
        210                 215                 220

Phe His Arg Pro Pro Arg Ser Pro Leu Ser Trp Gly Leu Leu Arg His
225                 230                 235                 240

Cys His Asp Gly Thr Asn Phe Phe Thr Gly Glu Ala Gly Val Arg Leu
                245                 250                 255

Asp Tyr Ile Ser Leu His Arg Lys Gly Ala Arg Ser Ser Ile Ser Ile
                260                 265                 270

Leu Glu Gln Glu Lys Val Val Ala Gln Gln Ile Arg Gln Leu Phe Pro
            275                 280                 285

Lys Phe Ala Asp Thr Pro Ile Tyr Asn Asp Glu Ala Asp Pro Leu Val
        290                 295                 300

Gly Trp Ser Leu Pro Gln Pro Trp Arg Ala Asp Val Thr Tyr Ala Ala
305                 310                 315                 320

Met Val Val Lys Val Ile Ala Gln His Gln Asn Leu Leu Leu Ala Asn
                325                 330                 335

Thr Thr Ser Ala Phe Pro Tyr Ala Leu Leu Ser Asn Asp Asn Ala Phe
```

-continued

```
                    340                 345                 350
Leu Ser Tyr His Pro His Pro Phe Ala Gln Arg Thr Leu Thr Ala Arg
            355                 360                 365
Phe Gln Val Asn Asn Thr Arg Pro Pro His Val Gln Leu Leu Arg Lys
        370                 375                 380
Pro Val Leu Thr Ala Met Gly Leu Leu Ala Leu Leu Asp Glu Glu Gln
385                 390                 395                 400
Leu Trp Ala Glu Val Ser Gln Ala Gly Thr Val Leu Asp Ser Asn His
                405                 410                 415
Thr Val Gly Val Leu Ala Ser Ala His Arg Pro Gln Gly Pro Ala Asp
            420                 425                 430
Ala Trp Arg Ala Ala Val Leu Ile Tyr Ala Ser Asp Asp Thr Arg Ala
            435                 440                 445
His Pro Asn Arg Ser Val Ala Val Thr Leu Arg Leu Arg Gly Val Pro
    450                 455                 460
Pro Gly Pro Gly Leu Val Tyr Val Thr Arg Tyr Leu Asp Asn Gly Leu
465                 470                 475                 480
Cys Ser Pro Asp Gly Glu Trp Arg Arg Leu Gly Arg Pro Val Phe Pro
                485                 490                 495
Thr Ala Glu Gln Phe Arg Arg Met Arg Ala Ala Glu Asp Pro Val Ala
            500                 505                 510
Ala Ala Pro Arg Pro Leu Pro Ala Gly Gly Arg Leu Thr Leu Arg Pro
            515                 520                 525
Ala Leu Arg Leu Pro Ser Leu Leu Leu Val His Val Cys Ala Arg Pro
    530                 535                 540
Glu Lys Pro Pro Gly Gln Val Thr Arg Leu Arg Ala Leu Pro Leu Thr
545                 550                 555                 560
Gln Gly Gln Leu Val Leu Val Trp Ser Asp Glu His Val Gly Ser Lys
                565                 570                 575
Cys Leu Trp Thr Tyr Glu Ile Gln Phe Ser Gln Asp Gly Lys Ala Tyr
            580                 585                 590
Thr Pro Val Ser Arg Lys Pro Ser Thr Phe Asn Leu Phe Val Phe Ser
        595                 600                 605
Pro Asp Thr Gly Ala Val Ser Gly Ser Tyr Arg Val Arg Ala Leu Asp
    610                 615                 620
Tyr Trp Ala Arg Pro Gly Pro Phe Ser Asp Pro Val Pro Tyr Leu Glu
625                 630                 635                 640
Val Pro Val Pro Arg Gly Pro Pro Ser Pro Gly Asn Pro
                645                 650
```

What is claimed:

1. A purified human recombinant α-L-iduronidase having a purity of greater than about 99%, wherein said purified human recombinant α-L-iduronidase comprises the amino acid sequence of residues 26 to 653 of SEQ ID NO:2.

2. A pharmaceutical composition comprising the human recombinant α-L-iduronidase of claim 1 and a pharmaceutically acceptable carrier.

3. The pharmaceutical composition of claim 2 further comprising a sodium chloride solution, a buffer and human albumin.

4. The pharmaceutical composition of claim 2 wherein said human recombinant α-L-iduronidase is present at a concentration of about 0.05 to 0.20 mg/mL or about 12,500 to about 50,000 units per mL.

5. The pharmaceutical composition of claim 3 wherein said human albumin is present at a concentration of at least about 1 mg/mL.

6. The pharmaceutical composition of claim 3 wherein said buffer is a sodium phosphate buffer at a concentration of about 10–50 mM.

7. The pharmaceutical composition of claim 3 wherein the pH of said sodium chloride solution is about 5.8.

* * * * *

UNITED STATES PATENT AND TRADEMARK OFFICE
CERTIFICATE OF CORRECTION

PATENT NO.    : 6,426,208 B1
DATED         : July 30, 2002
INVENTOR(S)   : Emil Kakkis et al.

It is certified that error appears in the above-identified patent and that said Letters Patent is hereby corrected as shown below:

Drawings,
Delete drawing sheets 11, 12 and 15, and substitute therefor the drawing sheets 11, 12 and 15, consisting of drawing Figs. 4, 5 and 8, as shown on the attached sheets.

Signed and Sealed this

Seventh Day of January, 2003

JAMES E. ROGAN
*Director of the United States Patent and Trademark Office*